United States Patent
Lewis et al.

(10) Patent No.: US 9,714,273 B2
(45) Date of Patent: Jul. 25, 2017

(54) EXPRESSION SYSTEMS AND ASSOCIATED METHODS

(71) Applicants: Randolph V. Lewis, Nibley, UT (US); Dong Chen, Logan, UT (US); Justin A. Jones, Nibley, UT (US); Sreevidhya T. Krishnaji, Chapel Hill, NC (US); Paula F. Oliveira, North Logan, UT (US); Gargi Bhattacharyya, Farmington, UT (US)

(72) Inventors: Randolph V. Lewis, Nibley, UT (US); Dong Chen, Logan, UT (US); Justin A. Jones, Nibley, UT (US); Sreevidhya T. Krishnaji, Chapel Hill, NC (US); Paula F. Oliveira, North Logan, UT (US); Gargi Bhattacharyya, Farmington, UT (US)

(73) Assignee: Utah State University, Logan, UT (US)

( * ) Notice: Subject to any disclaimer, the term of this patent is extended or adjusted under 35 U.S.C. 154(b) by 0 days.

(21) Appl. No.: 14/879,046

(22) Filed: Oct. 8, 2015

(65) Prior Publication Data

US 2016/0102125 A1   Apr. 14, 2016

Related U.S. Application Data

(60) Provisional application No. 62/061,574, filed on Oct. 8, 2014.

(51) Int. Cl.
  *C12P 21/02* (2006.01)
  *C07K 14/435* (2006.01)
  *C12N 15/70* (2006.01)

(52) U.S. Cl.
  CPC .. *C07K 14/43563* (2013.01); *C07K 14/43518* (2013.01); *C12N 15/70* (2013.01)

(58) Field of Classification Search
  None
  See application file for complete search history.

(56) References Cited

U.S. PATENT DOCUMENTS

| | | | |
|---|---|---|---|
| 5,728,810 A | 3/1998 | Lewis et al. | |
| 5,733,771 A | 3/1998 | Lewis et al. | |
| 5,756,677 A | 5/1998 | Lewis et al. | |
| 5,989,894 A | 11/1999 | Lewis et al. | |
| 5,994,099 A | 11/1999 | Lewis et al. | |
| 6,410,270 B1* | 6/2002 | Strittmatter | C07K 16/2863 435/252.3 |
| 7,057,023 B2 | 6/2006 | Islam et al. | |
| 7,157,615 B2 | 1/2007 | Karatzas et al. | |
| 7,288,391 B2 | 10/2007 | Roth et al. | |
| 7,521,228 B2 | 4/2009 | Lewis et al. | |
| 7,723,109 B2 | 5/2010 | Lewis | |
| 9,321,816 B2 | 4/2016 | Lewis et al. | |
| 2007/0254335 A1 | 11/2007 | Shao et al. | |
| 2007/0260039 A1* | 11/2007 | Karatzas | C07K 14/43518 530/324 |
| 2011/0230911 A1 | 9/2011 | Scheibel et al. | |
| 2014/0093965 A1* | 4/2014 | Lewis | C12P 21/02 435/471 |
| 2015/0047532 A1 | 2/2015 | Lewis et al. | |
| 2015/0202651 A1 | 7/2015 | Lewis et al. | |
| 2015/0292120 A1 | 10/2015 | Lewis et al. | |

FOREIGN PATENT DOCUMENTS

| | | |
|---|---|---|
| WO | 2014052975 A1 | 4/2014 |
| WO | 2015023798 A1 | 2/2015 |
| WO | 2015095407 A2 | 6/2015 |

OTHER PUBLICATIONS

International Search Report and Written Opinion for PCT/US2015/054782, filed Oct. 8, 2015, mailing date Jan. 6, 2016.

\* cited by examiner

*Primary Examiner* — Jim Ketter

(57) ABSTRACT

A method of producing synthetic spider silk, including: transforming *Escherichia coli* with an expression vector; fermenting the transformed *E. coli* in a culture medium; inducing spider silk protein expression in the cultured *E. coli*; extracting the spider silk; and purifying the spider silk. Related vectors and genetically modified cells are also disclosed.

14 Claims, 31 Drawing Sheets

1: Protein ladder
2: Expressed pET19K-FLYS$_3$ protein (normalized to OD$_{600}$ = 10)
3: Expressed pET19K-SX-FLYS$_3$ protein (normalized to OD$_{600}$ = 10)

1: Protein ladder
2: Purified FLYS$_3$ protein 250mg/L in BioRad sample buffer
3: Before IPTG induction (normalized to OD$_{600}$ = 10)
4: 1 hour after IPTG induction (normalized to OD$_{600}$ = 10)
5: 2 hours after IPTG induction (normalized to OD$_{600}$ = 10)
6: 3 hours after IPTG induction (normalized to OD$_{600}$ = 10)

1: Protein ladder
2: Purified FLYS₃ protein 250mg/L in BioRad sample buffer
3: IPTG induced at 20 °C, 2 hours after induction (normalized to $OD_{600}$ = 10)
4: IPTG induced at 20 °C, 3 hours after induction (normalized to $OD_{600}$ = 10)
5: IPTG induced at 25 °C, 3 hours after induction (normalized to $OD_{600}$ = 10)
6: IPTG induced at 32 °C, 3 hours after induction (normalized to $OD_{600}$ = 10)

SEQ ID NO: 1

| | | | | | |
|---|---|---|---|---|---|
| agccgcctgg | cgagcccgga | tagcggcgcg | cgcgtggcga | gcgcggtgag | caacctggtg | 60
| agcagcggcc | cgaccagcag | cgcggcgctg | agcagcgtga | ttagcaacgc | ggtgagccag | 120
| attggcgcga | gcaacccggg | cctgagcggc | tgcgatgtgc | tgattcaggc | gctgctggaa | 180
| attgtgagcg | cgtgcgtgac | cattctgagc | agcagcagca | ttggccaggt | gaactatggc | 240
| gcggcgagcc | agtttgcgca | ggtggtgggc | cagagcgtgc | tgagcgcgtt | t | 291

FIG. 8

SEQ ID NO: 2

| | | | | | |
|---|---|---|---|---|---|
| ggtgccggtg | gttatggtcg | tggtgctggt | gcggtgccg | gtgcagcagc | tggtgccggt | 60 |
| gctggcgcag | gcggttatgg | tggtcagggt | ggctacggtg | ccggtgccgg | tgctggtgcc | 120 |
| gcagccgcag | cgggtgcggg | tgcaggcggt | gctggcggtt | atggcagagg | tgctggggct | 180 |
| ggtgcaggcg | ctgcagccgg | tgcgggtgct | ggtgcgggtg | gatatggtgg | ccagggtggt | 240 |
| tatggcgctg | gcgcaggggc | aggcgcagca | gcagcagctg | gggcaggcgc | aggcggtgcc | 300 |
| ggtggctatg | gacgcggagc | cggtgccggt | gcagggcag | cagcgggtgc | tggtgccggt | 360 |
| gcaggggtt | atggtggcca | aggcggatat | ggtgcgggtg | caggcgctgg | tgcagcagca | 420 |
| gccgctggtg | ccggtgccgg | tggtgcgggt | ggctacggaa | gaggtgcggg | tgccggtgcc | 480 |
| ggtgctgcag | cgggtgcggg | tgcgggtgcc | ggtggttatg | gcggtcaggg | tgggtatggt | 540 |
| gcgggtgctg | gtgcaggcgc | agctgcagcc | gctggtgctg | gtgcaggcgg | agccggtgga | 600 |
| tatggccgag | gtgctggcgc | aggcgctggc | gctgctgctg | gtgccggtgc | gggtgctggg | 660 |
| ggatacggtg | gtcaaggggg | ttatggtgcg | ggtgccggtg | cgggtgcagc | cgcagcagct | 720 |
| ggtgcgggtg | cgggtggtgc | aggggatat | ggccgtggtg | ccggtgctgg | tgcgggtgct | 780 |
| gcagccggtg | ctgggcagg | ggctggcggt | tatgggggtc | aaggcggtta | tggcgctggt | 840 |
| gctggtgctg | gggctgccgc | agcagccggt | gctggtgctg | gcggtgcggg | tggttacggt | 900 |
| cggggagctg | gcgctggtgc | tggcgcagca | gcgggtgccg | gtgctggtgc | cggtggctac | 960 |
| ggtggacaag | gtggctatgg | tgccggtgca | ggcgcagggg | ctgcagccgc | agccggtgcc | 1020 |
| ggtgccggtg | gcgctggggg | ttatggtcgc | ggagcgggtg | caggcgcagg | cgcagccgct | 1080 |
| ggcgctggtg | cgggtgctgg | cggttatggt | ggacaagggg | gttatggggc | tggtgctggc | 1140 |
| gcaggggcag | ctgctgcagc | gggtgctggc | gcttcc | | | 1176 |

FIG. 9

SEQ ID NO: 3

```
ggtgcaggtc agggtggtta tggtggtctg ggtagccagg gtgccggtcg tggtggactg      60
ggtggtcaag gtgctggtgc agcagcagct gccgcagcag caggcggtgc aggccaaggc     120
ggatatggcg gactggggttc acagggtgca ggccgtggcg gtttaggtgg tcaaggcgca    180
ggcgctgctg cagccgcagc ggcagcagct ggccaaggtg gctatggtgg cttaggctca    240
cagggtggcg gtgctggaca gggtggatac ggtggccttg gcagtcaagg tgcgggtcgc    300
ggtggtttag gcggtcaggg tgcgggtgcg gctgctgcag ctgcggcagc gggtggtgct    360
gggcaaggcg gttacggtgg attaggtagc caaggtgcag gacgcggagg tcttggtgga    420
cagggtgctg gcgctgctgc ggcagcagca gccgctgggg gtgctggtca aggggttat     480
ggcggtttag gatctcaggg tgcgggacgg ggtggtctgg gagggcaagg ggcaggcgca    540
gcagcagcgg cagctgcagc cggtggtgcc ggacaagggg gatatggggg tcttggctcc    600
caaggcgctg gtcgtggcgg tcttggaggc caaggtgccg gtgccgctgc agcggctgct    660
gctgcagcgg gtcaaggggg atacggtggt ctgggatcac aaggtggtgg cgcagggcaa    720
ggtggtatg ggggtttagg ttcgcaaggt gctggccgtg ggggactggg aggacagggt     780
gccggtgcgg cagccgctgc agctgctgcg ggtggcgctg gtcagggtgg ctatggcgga    840
ttgggctctc aagggggcagg tcgggtggc ttgggaggac aaggtgcggg tgcagccgct    900
gcggcagctg ccgctggcgg agcaggccag ggtggctacg gtggactggg ttcccaaggt    960
gcgggaagag gtggcttggg tggccagggt gcagggcag cggctgcagc ggcagcagcc    1020
```

FIG. 10

SEQ ID NO: 4

| | | | | | |
|---|---|---|---|---|---:|
| ccgggtcagc | agggtccggg | tggttatggt | cctggccagc | agggaccgag | cggtccgggt | 60 |
| agtgcagcag | cagctgcagc | agccgcaggc | cctggtcagc | aaggccctgg | tggatatgga | 120 |
| ccaggccaac | agggtcctgg | cggatacggt | cctggtcaac | aaggtccgtc | aggtccgggt | 180 |
| tcagccgcag | cggctgctgc | cgcagcaggt | ccaggtggct | acggaccggg | tcaacaggga | 240 |
| cccggtgggt | acggaccagg | acagcaaggg | ccaggcggtt | atggccctgg | acaacaaggg | 300 |
| cctagtggtc | ctggttctgc | agcggcagcc | gctgcggcag | ctggtccggg | acagcaagga | 360 |
| cccggtggat | acggtcccgg | tcagcaggga | cctggcggtt | acggacccgg | acaacaggt | 420 |
| ccatctggtc | ctggtagcgc | agccgcagca | gcagcggctg | caggtccagg | acaacaaggt | 480 |
| cctggtgggt | atggtccagg | gcagcaaggt | ccgagtggtc | caggctctgc | ggcagcggca | 540 |
| gcagcagcag | cgggacctgg | tcaacagggt | ccaggggat | atggcccagg | tcagcaagga | 600 |
| ccgggtggct | atgggccagg | tcaacaaggc | cctagcggtc | cgggatctgc | cgcagctgca | 660 |
| gcggcagcgg | caggtcctgg | cggttatgga | ccaggtcagc | agggtcccgg | tggctacggt | 720 |
| cccggacaac | aaggcccagg | gggttacgga | cctggccagc | aaggtccttc | tggaccggga | 780 |
| agcgctgcag | ccgcagcagc | tgcagccggt | ccaggccagc | aagggcctgg | gggttacggt | 840 |
| ccgggtcagc | aaggcccagg | cggatacggt | ccaggacaac | agggaccaag | tggtccggga | 900 |
| tcagcagccg | ctgccgcagc | ggcagccggt | ccggtcaac | aaggacctgg | tggctacggt | 960 |
| cctgggcaac | agggtcctag | cggtccaggg | tcagcagcag | cagccgcagc | tgcagca | 1017 |

FIG. 11

SEQ ID NO: 5

| | | | | | |
|---|---|---|---|---|---:|
| aagcttcata | tgggatcaac | cggtccgggg | ggtccgggtg | gttatggtcc | tggtggtagt | 60 |
| ggtccaggtg | gctatggacc | gggtggttcc | ggtccaggcg | gttatggccc | tggcggttca | 120 |
| ggtccgggtg | gatacggacc | aggtggcagc | ggtccgagtg | gtccgggtag | tgcagcagca | 180 |
| gcagccgcag | ctgcaggtcc | aggggatat | ggtccagggg | gtagcggacc | tggcggttat | 240 |
| gggccaggtg | gctctggccc | tggtggatat | ggcccaggcg | gaagtggccc | aggtggttac | 300 |
| ggacctgggg | gatcaggacc | aggcggttac | ggtccgggtg | gctcaggtcc | tagcggtccg | 360 |
| ggttcagccg | cagcggcagc | agcagcggca | ggaccgggtg | gctatggcc | agggggttcg | 420 |
| ggacctggtg | gttatggacc | tggcggaagc | ggtcctgggg | gttacggtcc | aggtggaagt | 480 |
| ggaccgtcag | gtccaggtag | cgcagctgcc | gctgcagccg | cagcaggtcc | aggtgggtac | 540 |
| ggtcctggtg | gttctggacc | gggtgggtat | ggtccgggtg | gaagcggacc | gggtggatat | 600 |
| ggccctgggg | gatctggtcc | tggcggatat | ggacctggtg | ggtcgggacc | aggggatac | 660 |
| ggaccgggtg | gtagtggccc | aggcggatac | ggtcctggcg | gtagcggtcc | atcaggtccg | 720 |
| ggatctgctg | ctgctgcggc | agctgcagcc | ggaccagggg | gttatggacc | aggtggttca | 780 |
| ggaccaggtg | gctacggtcc | aggcggtagt | gggcctgggg | gatatggtcc | gggtggctct | 840 |
| gggcctggcg | gttacggacc | tggcggtagt | ggaccgggtg | gttatggccc | aggtggctcc | 900 |
| ggtccgggtg | ggtatgggcc | aggtggatct | gggccaggcg | gttatggtcc | aggggatcg | 960 |
| ggtccaggtg | gatatggccc | aggtggttca | ggtccatctg | gtccgggttc | cgcagctgca | 1020 |
| gccgcagccg | cagcttccgg | agggcccgat | atcctcgagg | gatcc | | 1065 |

FIG. 12

SEQ ID NO: 6

```
ggccatcatc atcatcatca tcatcatcat cacagcagcg gccatatcga cgacgacgac      60
aagcatatgc tcgaggatcc gggaagcgct agccgctgg cgagccgga tagcggcgcg       120
cgcgtggcga gcgcggtgag caacctggtg agcagcggcc cgaccagcag cgcggcgctg     180
agcagcgtga ttagcaacgc ggtgagccag attggcgcga gcaaccgggg cctgagcggc     240
tgcgatgtgc tgattcaggc gctgctggaa attgtgagcg cgtcgtgac cattctgagc      300
agcagcagca ttggccaggt gaactatggc gcggcgagcc agtttgcgca ggtggtgggc     360
cagagcgtgc tgagcgcgtt tgctgcttga taagcccgaa aggaagctga gttggctgct    420
gccaccgctg agcaataact agcataaccc cttggggcct ctaaacgggt cttgagggt     480
ttttttgctga aaggaggaac tatatccgga ttggcgaatg ggacgcgccc tgtagcggcg   540
cattaagcgc ggcgggtgtg gtggttacgc gcagcgtgac cgctacactt gccagcgccc    600
tagcgcccgc tcctttcgct ttcttccctt cctttctcgc cacgttcgcc ggctttcccc    660
gtcaagctct aaatcggggg ctcccttttag ggttccgatt tagtgcttta cggcacctcg   720
accccaaaaa acttgattag ggtgatggtt cacgtagtgg gccatcgccc tgatagacgg    780
ttttttcgccc tttgacgttg gagtccacgt tctttaatag tggactcttg ttccaaactg    840
gaacaacact caacctatc tcggtctatt cttttgattt ataagggatt ttgccgattt     900
cggcctattg gttaaaaaaat gagctgattt aacaaaaatt taacgcgaat tttaacaaaa    960
tattaacgtt tacaatttca ggtggcactt ttcggggaaa tgtgcgcgga acccctattt    1020
gtttattttt ctaaatacat tcaaatatgt atccgctcat gaattaattc ttagaaaaac    1080
tcatcgagca tcaaatgaaa ctgcaattta ttcatatcag gattatcaat accatatttt    1140
tgaaaaagcc gtttctgtaa tgaaggagaa aactcaccga ggcagttcca taggatggca   1200
agatcctggt atcggtctgc gattccgact cgtccaacat caatacaacc tattaattc    1260
ccctcgtcaa aataaggtt atcaagtgag aaatcaccat gagtgacgac tgaatccggt    1320
gagaatggca aaagtttatg catttcttc cagacttgtt caacaggcca gccattacgc    1380
tcgtcatcaa aatcactcgc atcaaccaaa ccgttattca ttcgtgattg cgcctgagcg   1440
agacgaaata cgcgatcgct gttaaaagga caattacaaa caggaatcga atgcaaccgg   1500
cgcaggaaca ctgccagcgc atcaacaata ttttcacctg aatcaggata ttcttctaat   1560
acctggaatg ctgttttccc ggggatcgca gtggtgagta accatgcatc atcaggagta   1620
cggataaaat gcttgatggt cggaagaggc ataaattccg tcagccagtt tagtctgacc   1680
atctcatctg taacatcatt ggcaacgcta cctttgccat gtttcagaaa caactctggc   1740
gcatcgggct tcccatacaa tcgatagatt gtcgcacctg attgcccgac attatcgcga   1800
gcccatttat acccatataa atcagcatcc atgttggaat ttaatcgcgg cctagagcaa   1860
gacgtttccc gttgaatatg gctcataaca cccttgtat tactgtttat gtaagcagac   1920
agttttattg ttcatgacca aaatccctta acgtgagttt tcgttccact gagcgtcaga   1980
ccccgtagaa aagatcaaag gatcttcttg agatcctttt ttctgcgcg taatctgctg    2040
cttgcaaaca aaaaaaccac cgctaccagc ggtggtttgt ttgccggatc aagagctacc   2100
aactcttttt ccgaaggtaa ctggcttcag cagagcgcag ataccaaata ctgtccttct   2160
agtgtagccg tagttaggcc accacttcaa gaactctgta gcaccgccta catacctcgc   2220
tctgctaatc ctgttaccag tggctgctgc cagtggcgat aagtcgtgtc ttaccgggtt   2280
ggactcaaga cgatagttac cggataaggc gcagcggtcg ggctgaacgg ggggttcgtg   2340
cacacagccc agcttggagc gaacgaccta ccgaactg agatacctac agcgtgagct    2400
atgagaaagc gccacgcttc ccgaagggag aaaggcggac aggtatccgg taagcggcag   2460
ggtcggaaca ggagagcgca cgagggagct ccaggggga aacgcctggt atctttatag   2520
tcctgtcggg tttcgccacc tctgacttga gcgtcgattt ttgtgatgct cgtcaggggg   2580
gcggagccta tggaaaaacg ccagcaacgc ggccttttta cggttcctgg ccttttgctg   2640
gccttttgct cacatgttct tcctgcgtt atccctgat tctgtggata accgtattac    2700
cgcctttgag tgagctgata ccgctcgccg cagccgaacg accgagcgca gcgagtcagt   2760
gagcgaggaa gcggaagagc gcctgatgcg gtattttctc cttacgcatc tgtgcggtat   2820
ttcacaccgc atatatggtg cactctcagt acaatctgct ctgatgccg atagttaagc   2880
cagtatacac tccgctatcg ctacgtgact gggtcatggc tgcgccccga cacccgccaa   2940
cacccgctga cgcgccctga cgggcttgtc tgctcccggc atccgcttac agacaagctg   3000
tgaccgtctc cgggagctgc atgtgtcaga ggttttcacc gtcatcaccg aaacgcgcga   3060
```

*FIG. 13*

SEQ ID NO: 6 (continued)

```
ggcagctgcg gtaaagctca tcagcgtggt cgtgaagcga ttcacagatg tctgcctgtt   3120
catccgcgtc cagctcgttg agtttctcca gaagcgttaa tgtctggctt ctgataaagc   3180
gggccatgtt aagggcggtt ttttcctgtt tggtcactga tgcctccgtg taagggggat   3240
ttctgttcat gggggtaatg ataccgatga aacgagagag gatgctcacg ataccggtta   3300
ctgatgatga acatgcccgg ttactggaac gttgtgaggg taaacaactg gcggtatgga   3360
tgcggcggga ccagagaaaa atcactcagg gtcaatgcca gcgcttcgtt aatacagatg   3420
taggtgttcc acagggtagc cagcagcatc ctgcgatgca gatccggaac ataatggtgc   3480
agggcgctga cttccgcgtt tccagacttt acgaaacacg gaaaccgaag accattcatg   3540
ttgttgctca ggtcgcagac gttttgcagc agcagtcgct tcacgttcgc tcgcgtatcg   3600
gtgattcatt ctgctaacca gtaaggcaac cccgccagcc tagccgggtc ctcaacgaca   3660
ggagcacgat catgcgcacc cgtggccagg acccaacgct gcccgagatg cgccgcgtgc   3720
ggctgctgga gatggcggac gcgatggata tgttctgcca agggttggtt tgcgcattca   3780
cagttctccg caagaattga ttggctccaa ttcttggagt ggtgaatccg ttagcgaggt   3840
gccgccggct tccattcagt cgaggtggc ccggctccat gcaccgcgac gcaacgcggg   3900
gaggcagaca aggtataggg cggcgcctac aatccatgcc aaccgttcc atgtgctcgc   3960
cgaggcggca taaatcgccg tgacgatcag cggtccagtg atcgaagtta ggctggtaag   4020
agccgcgagc gatccttgaa gctgtcctg atggtcgtca tctacctgcc tggacagcat   4080
ggcctgcaac gcgggcatcc cgatgccgcc ggaagcgaga agaatcataa tggggaaggc   4140
catccagcct cgcgtcgcga acgccagcaa gacgtagccc agcgcgtcgg ccgccatgcc   4200
ggcgataatg gcctgcttct cgccgaaacg tttggtggcg ggaccagtga cgaaggcttg   4260
agcgagggcg tgcaagattc cgaataccgc aagcgacagg ccgatcatcg tcgcgctcca   4320
gcgaaagcgg tcctcgccga aaatgaccca gagcgctgcc ggcacctgtc ctacgagttg   4380
catgataaag aagacagtca taagtgcggc gacgatagtc atgccccgcg cccaccggaa   4440
ggagctgact gggttgaagg ctctcaaggg catcggtcga gatcccggtg cctaatgagt   4500
gagctaactt acattaattg cgttgcgctc actgcccgct ttccagtcgg gaaacctgtc   4560
gtgccagctg cattaatgaa tcggccaacg cgcgggagag gcggtttgc gtattgggcg   4620
ccagggtggt ttttcttttc accagtgaga cgggcaacag ctgattgccc ttcaccgcct   4680
ggccctgaga gagttgcagc aagcggtcca cgctggtttg cccagcagg cgaaaatcct   4740
gtttgatggt ggttaacggc gggatataac atgagctgtc ttcggtatcg tcgtatccca   4800
ctaccgagat atccgcacca acgcgcagcc cggactcggt aatggcgcgc attgcgccca   4860
gcgccatctg atcgttgaca accagatcg cagtgggaac gatgccctca ttcagcattt   4920
gcatggtttg ttgaaaaccg gacatggcac tccagtcgcc ttcccgttcc gctatcggct   4980
gaatttgatt gcgagtgaga tatttatgcc agccagccag acgcagacgc gccgagacag   5040
aacttaatgg gcccgctaac agcgcgattt gctggtgacc caatgcgacc agatgctcca   5100
cgcccagtcg cgtaccgtct tcatgggaga aaataatact gttgatggt gtctggtcag   5160
agacatcaag aaataacgcc ggaacattag tgcaggcagc ttccacagca atggcatcct   5220
ggtcatccag cggatagtta atgatcagcc cactgacgcg ttgcgcgaga gattgtgca   5280
ccgccgcttt acaggcttcg acgccgcttc gttctaccat cgacaccacc acgctggcac   5340
ccagttgatc ggcgcgagat ttaatcgccg cgacaatttg cgacggcgcg tgcagggcca   5400
gactggaggt ggcaacgcca atcagcaacg actgtttgcc cgccagttgt tgtgccacgc   5460
ggttgggaat gtaattcagc tccgccatcg ccgcttccac ttttcccgc gttttcgcag   5520
aaacgtggct ggcctggttc accacgcggg aaacggtctg ataagagaca ccggcatact   5580
ctgcgacatc gtataacgtt                                                5600
```

FIG. 13 (continued)

SEQ ID NO. 7

```
atccggatat agttcctcct ttcagcaaaa aaccctcaa gacccgttta gaggcccaa      60
ggggttatgc tagttattcg ctcagcggtg gcagcagcca actcagcttc ctttcgggct   120
tatcaagcag caaacgcgct cagcacgctc tggcccacca cctgcgcaaa ctggctcgcc   180
gcgccatagt tcacctggcc aatgctgctg ctgctcagaa tggtcacgca cgcgctcaca   240
atttccagca gcgcctgaat cagcacatcg cagccgctca ggcccgggtt gctcgcgcca   300
atctggctca ccgcgttgct aatcacgctg ctcagcgccg cgctgctggt cgggccgctg   360
ctcccaggtt gctcaccgcg ctcgccacgc gcgcgcgct atccgggctc gccaggcggc   420
tagcgcttcc cggatcctcg agcatatgct tgtcgtcgtc gtcgatatgg ccgctgctgt   480
gatgatgatg atgatgatga tgatgatggc ccatggtata tctccttctt aaagttaaac   540
aaaattattt ctagagggga attgttatcc gctcacaatt cccctatagt gagtcgtatt   600
aatttcgcgg gatcgagatc tgacctgtta tcgcacaatg attcggttat actgttcgcc   660
gttgtccaac aggaccgcct ataaaggcca aaatttat tgttagctga gtcaggagat    720
gcggatgtta aagcgtgaaa tgaacattgc cgattatgat gccgaactgt ggcaggctat   780
ggagcaggaa aaagtacgtc aggaagagca catcgaactg atcgcctccg aaaactacac   840
cagcccgcgc gtaatgcagg cgcagggttc tcagctgacc aacaaatatg ctgaaggtta   900
tccgggcaaa cgctactacg gcggttgcga gtatgttgat atcgttgaac aactggcgat   960
cgatcgtgcg aaagaactgt tcggcgctga ctacgctaac gtccagccgc actccggctc  1020
ccaggctaac tttgcggtct acacccgcct gctggaacca ggtgatacacg ttctgggtat  1080
gaacctggcg catgcggtc acctgactca cggttctccg gttaacttct ccggtaaact   1140
gtacaacatc gttccttacg gtatcgatgc taccggtcat atcgactacg ccgatctgga  1200
aaaacaagcc aaagaacaca agccgaaaat gattatcggt ggtttctctg catattccgg  1260
cgtggtggac tgggcgaaaa tgcgtgaaat cgctgacagc atcggtgctt acctgttcgt  1320
tgatatggcg cacgttgcgg gctggttgc tgctggcgtc tacccgaacc cggttcctca   1380
tgctcacgtt gttactacca ccactcacaa aaccctggcg ggtccgcgcg gcggcctgat  1440
cctggcgaaa ggtggtagcg aagagctgta caaaaactg aactctgccg ttttccctgg   1500
tggtcagggc ggtccgttga tgcacgtaat cgccggtcgcg gcggttgctc tgaaagaagc  1560
gatggagcct gagttcaaaa cttaccagca gcaggtcgcg aaaaacgcta aagcgatggt  1620
agaagtgttc ctcgagcgcg gctacaaagt ggtttccggc ggcactgata accacctgtt  1680
cctggttgat ctggttgata aaacctgac cggtaaagaa gcagacgccg ctctgggccg   1740
tgctaacatc accgtcaaca aaaacagcgt accgaacgat ccgaagagcc cgtttgtgac  1800
ctccggtatt cgcgtgggta ctccggcaat tacgcgtcgc ggcttcaaag aagcagaagc  1860
gaaagaactg gctggctgga tgtgtgacgt gctggacagc atcaatgatg aagccgttat  1920
cgagcgcatc aaaggtaaag ttctcgacat ctgcgcacgt taccggttt acgcataagc   1980
gaaacggtga tttgctgaca atgtgctcgt tgttcatgtt ggatgcggca tgaacacgtc  2040
gaccgtagcc cgagacgata agttcgctta ccggctcgaa tgaagagagc ttctctcgat  2100
attcagt                                                            2107
```

FIG. 14

SEQ ID NO: 8

Ser Arg Leu Ala Ser Pro Asp Ser Gly Ala Arg Val Ala Ser Ala Val
1               5                   10                  15

Ser Asn Leu Val Ser Ser Gly Pro Thr Ser Ser Ala Ala Leu Ser Ser
                20                  25                  30

Val Ile Ser Asn Ala Val Ser Gln Ile Gly Ala Ser Asn Pro Gly Leu
        35                  40                  45

Ser Gly Cys Asp Val Leu Ile Gln Ala Leu Leu Glu Ile Val Ser Ala
        50                  55                  60

Cys Val Thr Ile Leu Ser Ser Ser Ser Ile Gly Gln Val Asn Tyr Gly
65                  70                  75                  80

Ala Ala Ser Gln Phe Ala Gln Val Val Gly Gln Ser Val Leu Ser Ala
                85                  90                  95

Phe

*FIG. 15*

SEQ ID NO: 9

Gly Ala Gly Gly Tyr Gly Arg Gly Ala Gly Ala Gly Ala Ala
1               5                   10                  15

Ala Gly Ala Gly Ala Gly Ala Gly Gly Tyr Gly Gly Gln Gly Gly Tyr
            20                  25                  30

Gly Ala Gly Ala Gly Ala Gly Ala Ala Ala Ala Gly Ala Gly Ala
            35                  40                  45

Gly Gly Ala Gly Gly Tyr Gly Arg Gly Ala Gly Ala Gly Ala
        50              55                  60

Ala Ala Gly Ala Gly Ala Gly Ala Gly Gly Tyr Gly Gly Gln Gly Gly
65              70                  75                  80

Tyr Gly Ala Gly Ala Gly Ala Gly Ala Ala Ala Ala Gly Ala Gly
            85                  90                  95

Ala Gly Gly Ala Gly Gly Tyr Gly Arg Gly Ala Gly Ala Gly Ala Gly
            100                 105                 110

Ala Ala Ala Gly Ala Gly Ala Gly Ala Gly Gly Tyr Gly Gly Gln Gly
        115                 120                 125

Gly Tyr Gly Ala Gly Ala Gly Ala Gly Ala Ala Ala Ala Gly Ala
    130                 135                 140

Gly Ala Gly Gly Ala Gly Gly Tyr Gly Arg Gly Ala Gly Ala Gly Ala
145                 150                 155                 160

Gly Ala Ala Ala Gly Ala Gly Ala Gly Ala Gly Gly Tyr Gly Gly Gln
                165                 170                 175

Gly Gly Tyr Gly Ala Gly Ala Gly Ala Gly Ala Ala Ala Ala Gly
            180                 185                 190

FIG. 16

SEQ ID NO: 9 (continued)

```
Ala Gly Ala Gly Gly Ala Gly Gly Tyr Gly Arg Gly Ala Gly Ala Gly
        195                 200                 205

Ala Gly Ala Ala Ala Gly Ala Gly Ala Gly Ala Gly Gly Tyr Gly Gly
        210                 215                 220

Gln Gly Gly Tyr Gly Ala Gly Ala Gly Ala Gly Ala Ala Ala Ala Ala
225             230                 235                 240

Gly Ala Gly Ala Gly Gly Ala Gly Gly Tyr Gly Arg Gly Ala Gly Ala
                245                 250                 255

Gly Ala Gly Ala Ala Ala Gly Ala Gly Ala Gly Ala Gly Gly Tyr Gly
                260                 265                 270

Gly Gln Gly Gly Tyr Gly Ala Gly Ala Gly Ala Gly Ala Ala Ala Ala
        275                 280                 285

Ala Gly Ala Gly Ala Gly Gly Ala Gly Gly Tyr Gly Arg Gly Ala Gly
        290                 295                 300

Ala Gly Ala Gly Ala Ala Ala Gly Ala Gly Ala Gly Ala Gly Gly Tyr
305                 310                 315                 320

Gly Gly Gln Gly Gly Tyr Gly Ala Gly Ala Gly Ala Gly Ala Ala Ala
                325                 330                 335

Ala Ala Gly Ala Gly Ala Gly Gly Ala Gly Gly Tyr Gly Arg Gly Ala
                340                 345                 350

Gly Ala Gly Ala Gly Ala Ala Ala Gly Ala Gly Ala Gly Ala Gly Gly
        355                 360                 365

Tyr Gly Gly Gln Gly Gly Tyr Gly Ala Gly Ala Gly Ala Gly Ala Ala
        370                 375                 380

Ala Ala Ala Gly Ala Gly Ala Ser
385             390
```

FIG. 16 (continued)

SEQ ID NO: 10

Gly Ala Gly Gln Gly Gly Tyr Gly Gly Leu Gly Ser Gln Gly Ala Gly
1               5                   10                  15

Arg Gly Gly Leu Gly Gly Gln Gly Ala Gly Ala Ala Ala Ala Ala Ala
                20                  25                  30

Ala Ala Gly Gly Ala Gly Gln Gly Gly Tyr Gly Gly Leu Gly Ser Gln
        35                  40                  45

Gly Ala Gly Arg Gly Gly Leu Gly Gly Gln Gly Ala Gly Ala Ala Ala
        50                  55                  60

Ala Ala Ala Ala Ala Ala Gly Gln Gly Gly Tyr Gly Gly Leu Gly Ser
65                  70                  75                  80

Gln Gly Gly Gly Ala Gly Gln Gly Gly Tyr Gly Gly Leu Gly Ser Gln
                85                  90                  95

Gly Ala Gly Arg Gly Gly Leu Gly Gly Gln Gly Ala Gly Ala Ala Ala
                100                 105                 110

Ala Ala Ala Ala Ala Gly Gly Ala Gly Gln Gly Gly Tyr Gly Gly Leu
            115                 120                 125

Gly Ser Gln Gly Ala Gly Arg Gly Gly Leu Gly Gly Gln Gly Ala Gly
    130                 135                 140

Ala Ala Ala Ala Ala Ala Ala Ala Gly Gly Ala Gly Gln Gly Gly Tyr
145                 150                 155                 160

Gly Gly Leu Gly Ser Gln Gly Ala Gly Arg Gly Gly Leu Gly Gly Gln
            165                 170                 175

Gly Ala Gly Ala Ala Ala Ala Ala Ala Ala Gly Gly Ala Gly Gln
        180                 185                 190

Gly Gly Tyr Gly Gly Leu Gly Ser Gln Gly Ala Gly Arg Gly Gly Leu
        195                 200                 205

*FIG. 17*

SEQ ID NO: 10 (continued)

Gly Gly Gln Gly Ala Gly Ala Ala Ala Ala Ala Ala Ala Ala Gly
    210             215                 220

Gln Gly Gly Tyr Gly Gly Leu Gly Ser Gln Gly Gly Ala Gly Gln
225             230              235                 240

Gly Gly Tyr Gly Gly Leu Gly Ser Gln Gly Ala Gly Arg Gly Gly Leu
            245              250                 255

Gly Gly Gln Gly Ala Gly Ala Ala Ala Ala Ala Ala Ala Gly Gly
            260              265                 270

Ala Gly Gln Gly Gly Tyr Gly Gly Leu Gly Ser Gln Gly Ala Gly Arg
        275              280                 285

Gly Gly Leu Gly Gly Gln Gly Ala Gly Ala Ala Ala Ala Ala Ala
        290              295                 300

Ala Gly Gly Ala Gly Gln Gly Gly Tyr Gly Gly Leu Gly Ser Gln Gly
305             310              315                 320

Ala Gly Arg Gly Gly Leu Gly Gly Gln Gly Ala Gly Ala Ala Ala Ala
            325              330                 335

Ala Ala Ala Ala
        340

FIG. 17 (continued)

SEQ ID NO: 11

Pro Gly Gln Gln Gly Pro Gly Gly Tyr Gly Pro Gly Gln Gln Gly Pro
1               5                   10                  15

Ser Gly Pro Gly Ser Ala Ala Ala Ala Ala Ala Ala Ala Gly Pro Gly
            20                  25                  30

Gln Gln Gly Pro Gly Gly Tyr Gly Pro Gly Gln Gln Gly Pro Gly Gly
            35                  40                  45

Tyr Gly Pro Gly Gln Gln Gly Pro Ser Gly Pro Gly Ser Ala Ala Ala
    50                  55                  60

Ala Ala Ala Ala Ala Gly Pro Gly Gly Tyr Gly Pro Gly Gln Gln Gly
65                  70                  75                  80

Pro Gly Gly Tyr Gly Pro Gly Gln Gln Gly Pro Gly Gly Tyr Gly Pro
                85                  90                  95

Gly Gln Gln Gly Pro Ser Gly Pro Gly Ser Ala Ala Ala Ala Ala Ala
            100                 105                 110

Ala Ala Gly Pro Gly Gln Gln Gly Pro Gly Gly Tyr Gly Pro Gly Gln
            115                 120                 125

Gln Gly Pro Gly Gly Tyr Gly Pro Gly Gln Gln Gly Pro Ser Gly Pro
            130                 135                 140

Gly Ser Ala Ala Ala Ala Ala Ala Ala Ala Gly Pro Gly Gln Gln Gly
145                 150                 155                 160

Pro Gly Gly Tyr Gly Pro Gly Gln Gln Gly Pro Ser Gly Pro Gly Ser
                165                 170                 175

Ala Ala Ala Ala Ala Ala Ala Ala Gly Pro Gly Gln Gln Gly Pro Gly
            180                 185                 190

*FIG. 18*

SEQ ID NO: 11 (continued)

Gly Tyr Gly Pro Gly Gln Gln Gly Pro Gly Gly Tyr Gly Pro Gly Gln
         195                 200                 205

Gln Gly Pro Ser Gly Pro Gly Ser Ala Ala Ala Ala Ala Ala Ala Ala
         210                 215                 220

Gly Pro Gly Gly Tyr Gly Pro Gly Gln Gln Gly Pro Gly Gly Tyr Gly
225                 230                 235                 240

Pro Gly Gln Gln Gly Pro Gly Gly Tyr Gly Pro Gly Gln Gln Gly Pro
             245                 250                 255

Ser Gly Pro Gly Ser Ala Ala Ala Ala Ala Ala Ala Ala Gly Pro Gly
             260                 265                 270

Gln Gln Gly Pro Gly Gly Tyr Gly Pro Gly Gln Gln Gly Pro Gly Gly
             275                 280                 285

Tyr Gly Pro Gly Gln Gln Gly Pro Ser Gly Pro Gly Ser Ala Ala Ala
         290                 295                 300

Ala Ala Ala Ala Ala Gly Pro Gly Gln Gln Gly Pro Gly Gly Tyr Gly
305                 310                 315                 320

Pro Gly Gln Gln Gly Pro Ser Gly Pro Gly Ser Ala Ala Ala Ala Ala
             325                 330                 335

Ala Ala Ala

FIG. 18 (continued)

SEQ ID NO: 12

Met Gly Ser Thr Gly Pro Gly Gly Pro Gly Gly Tyr Gly Pro Gly Gly
1               5                   10                  15

Ser Gly Pro Gly Gly Tyr Gly Pro Gly Gly Ser Gly Pro Gly Gly Tyr
            20                  25                  30

Gly Pro Gly Gly Ser Gly Pro Gly Gly Tyr Gly Pro Gly Gly Ser Gly
            35                  40                  45

Pro Ser Gly Pro Gly Ser Ala Ala Ala Ala Ala Ala Ala Ala Gly Pro
        50                  55                  60

Gly Gly Tyr Gly Pro Gly Gly Ser Gly Pro Gly Gly Tyr Gly Pro Gly
65              70                  75                  80

Gly Ser Gly Pro Gly Gly Tyr Gly Pro Gly Gly Ser Gly Pro Gly Gly
                85                  90                  95

Tyr Gly Pro Gly Gly Ser Gly Pro Gly Gly Tyr Gly Pro Gly Gly Ser
            100                 105                 110

Gly Pro Ser Gly Pro Gly Ser Ala Ala Ala Ala Ala Ala Ala Ala Gly
        115                 120                 125

Pro Gly Gly Tyr Gly Pro Gly Gly Ser Gly Pro Gly Gly Tyr Gly Pro
    130                 135                 140

Gly Gly Ser Gly Pro Gly Gly Tyr Gly Pro Gly Gly Ser Gly Pro Ser
145                 150                 155                 160

Gly Pro Gly Ser Ala Ala Ala Ala Ala Ala Ala Ala Gly Pro Gly Gly
            165                 170                 175

Tyr Gly Pro Gly Gly Ser Gly Pro Gly Gly Tyr Gly Pro Gly Gly Ser
            180                 185                 190

FIG. 19

SEQ ID NO: 12 (continued)

```
Gly Pro Gly Gly Tyr Gly Pro Gly Gly Ser Gly Pro Gly Gly Tyr Gly
            195                 200                 205

Pro Gly Gly Ser Gly Pro Gly Gly Tyr Gly Pro Gly Gly Ser Gly Pro
            210                 215                 220

Gly Gly Tyr Gly Pro Gly Gly Ser Gly Pro Ser Gly Pro Gly Ser Ala
225                 230                 235                 240

Ala Ala Ala Ala Ala Ala Ala Gly Pro Gly Gly Tyr Gly Pro Gly Gly
            245                 250                 255

Ser Gly Pro Gly Gly Tyr Gly Pro Gly Gly Ser Gly Pro Gly Gly Tyr
            260                 265                 270

Gly Pro Gly Gly Ser Gly Pro Gly Gly Tyr Gly Pro Gly Gly Ser Gly
            275                 280                 285

Pro Gly Gly Tyr Gly Pro Gly Gly Ser Gly Pro Gly Gly Tyr Gly Pro
            290                 295                 300

Gly Gly Ser Gly Pro Gly Gly Tyr Gly Pro Gly Gly Ser Gly Pro Gly
305                 310                 315                 320

Gly Tyr Gly Pro Gly Gly Ser Gly Pro Ser Gly Pro Gly Ser Ala Ala
            325                 330                 335

Ala Ala Ala Ala Ala Ala Ser Gly Gly Pro Asp Ile Leu Glu Gly Ser
            340                 345                 350
```

FIG. 19 (continued)

SEQ ID NO: 13

Gly Gly Ala Gly Gln Gly Gly Tyr Gly Gly Gln Gly Ala Gly Gln Gly
1               5                   10                  15

Gly Tyr Gly Gly Leu Gly Ser Gln Gly Ala Gly Arg Gly Gly Leu Gly
            20                  25                  30

Gly Gln Gly Ala Gly Ala Ala Ala Ala Ala Ala Ala Ala
        35              40                  45

FIG. 20

SEQ ID NO: 14

Ser Gly Pro Gly Gln Gln Gly Pro Gly Gly Tyr Gly Pro Gly Gln Gln
1               5                   10                  15

Gly Pro Gly Gly Tyr Gly Pro Gly Gln Gln Gly Pro Ser Gly Pro Gly
            20                  25                  30

Ser Ala Ala Ala Ala Ala Ala Ala Ala
        35              40

FIG. 21

SEQ ID NO: 15

Gly Ala Gly Ala Gly Gly Ala Gly Gly Tyr Gly Arg Gly Ala Gly Ala
1               5                   10                  15

Gly Ala Gly Ala Ala Ala Gly Ala Gly Ala Gly Ala Ala Ala Gly Ala
            20                  25                  30

Gly Ala Gly Gly Tyr Gly Gly Gln Gly Gly Tyr Gly Ala Gly Ala Gly
        35                  40                  45

Ala Gly Ala Ala Ala Ala Ala
    50              55

FIG. 22

SEQ ID NO: 16

```
Thr Thr Thr Thr Thr Ser Ala Ala Arg Ser Gln Ala Ala Ser Gln Ser
1               5                   10                  15

Ala Ser Ser Ser Tyr Ser Ser Ala Phe Ala Gln Ala Ala Ser Ser Ser
                20                  25                  30

Phe Ala Ile Ser Ser Ala Leu Ser Arg Ala Phe Ser Ser Val Ser Ser
            35                  40                  45

Ala Ser Ala Ala Ser Ser Leu Ala Tyr Ser Ile Gly Leu Ser Ala Ala
        50                  55                  60

Arg Ser Leu Gly Ile Ala Asp Ala Thr Leu Ala Gly Ala Leu Ala Arg
65                  70                  75                  80

Ala Val Gly Ala Leu Gly Gln Gly Ala Thr Ala Ala Ser Tyr Gly Asn
                85                  90                  95

Ala Leu Ser Thr Ala Ala Ala Gln Phe Phe Ala Thr Ala Gly Leu Leu
            100                 105                 110

Asn Ala Gly Asn Ala Ser Ala Leu Ala Ser Ser Phe Ala Arg Ala Phe
        115                 120                 125

Ser Ala Ser Ala Glu Ser Gln Ser Phe Ala Gln Ser Gln Ala Phe Gln
        130                 135                 140

Gln Ala Ser Ala Phe Gln Gln Ala Ala Ser Arg Ser Ala Ser Gln Ser
145                 150                 155                 160

Ala Ala Glu Ala Gly Ser Thr Ser Ser Ser
                165                 170
```

*FIG. 23*

SEQ ID NO: 17

| | | | | | | | | | | | | | | |
|---|---|---|---|---|---|---|---|---|---|---|---|---|---|---|
|Ser|Gly|Ala|Gly|Gly|Ser|Gly|Pro|Gly|Gly|Ala|Gly|Pro|Gly|Gly|Val|
|1| | | |5| | | |10| | | |15| |

Ser Gly Ala Gly Gly Ser Gly Pro Gly Gly Ala Gly Pro Gly Gly Val
1                  5                   10                  15

Gly Pro Gly Gly Ser Gly Pro Gly Gly Val Gly Pro Gly Gly Ser Gly
                 20                   25                  30

Pro Gly Gly Val Gly Pro Gly Gly Ser Gly Pro Gly Gly Val Gly Pro
             35                   40                  45

Gly Gly Ala Gly Gly Pro Tyr Gly Pro Gly Gly Ser Gly Pro Gly Gly
        50                  55                  60

Ala Gly Gly Ala Gly Gly Pro Gly Gly Ala Tyr Gly Pro Gly Gly Ser
65                  70                  75                  80

Tyr Gly Pro Gly Gly Ser Gly Gly Pro Gly Gly Ala Gly Gly Pro Tyr
             85                   90                  95

Gly Pro Gly Gly Glu Gly Pro Gly Gly Ala Gly Gly Pro Tyr Gly Pro
              100                105               110

Gly Gly Ala Gly Gly Pro Tyr Gly Pro Gly Gly Ala Gly Gly Pro Tyr
        115                 120                 125

Gly Pro Gly Gly Glu Gly Gly Pro Tyr Gly Pro Gly Gly Ser Tyr Gly
              130                135               140

Pro Gly Gly Ala Gly Gly Pro Tyr Gly Pro Gly Gly Pro Tyr Gly Pro
145                 150                155               160

Gly Gly Glu Gly Pro Gly Gly Ala Gly Gly Pro Tyr Gly Pro Gly Gly
           165                 170               175

Val Gly Pro Gly Gly Ser Gly Pro Gly Gly Tyr Gly Pro Gly Gly Ser
              180                185               190

Gly Pro Gly Gly Tyr Gly Pro Gly Gly Ala Gly Pro Gly Gly Tyr Gly
        195                200               205

Pro Gly Gly Ser Gly Pro Gly Gly Tyr Gly Pro Gly Gly Ser Gly Pro
        210                215               220

Gly Gly Tyr Gly Pro Gly Gly Ser Gly Pro Gly Gly Tyr Gly Pro Gly
225               230                235             240

Gly Ser Gly Pro Gly Gly Tyr Gly Ser Gly Gly Ala Gly Pro Gly Gly
             245                250               255

Tyr Gly Pro Gly Gly Ser Gly Pro Gly Gly Tyr Gly Pro Gly Gly Ser
              260                265               270

FIG. 24

SEQ ID NO: 17 (continued)

Gly Pro Gly Gly Tyr Gly Pro Gly Gly Thr Gly Pro Gly Gly Thr Gly
         275                 280                 285

Pro Gly Gly Ser Gly Pro Gly Gly Tyr Gly Pro Gly Gly Ser Gly Pro
     290                 295                 300

Gly Gly Ser Gly Pro Gly Gly Ser Gly Pro Gly Gly Tyr Gly Pro Ser
305                 310                 315                 320

Gly Ser Gly Pro Gly Gly Tyr Gly Pro Ser Gly Ser Gly Pro Gly Gly
             325                 330                 335

Tyr Gly Pro Gly Gly Ser Gly Pro Gly Gly Tyr Gly Pro Gly Gly Ser
             340                 345                 350

Gly Ala Gly Gly Thr Gly Pro Gly Gly Ala Gly Gly Ala Gly Gly Ala
         355                 360                 365

Gly Gly Ser Gly Gly Ala Gly Gly Ser Gly Gly Ala Gly Gly Ser Gly
         370                 375                 380

Gly Ala Gly Gly Ser Gly Gly Val Gly Gly Ser Gly Gly Thr Thr Ile
385                 390                 395                 400

Thr Glu Asp Leu Asp Ile Thr Ile Asp Gly Ala Asp Gly Pro Ile Thr
             405                 410                 415

Ile Ser Glu Glu Leu Thr Ile
             420

FIG. 24 (continued)

SEQ ID NO: 18

```
Arg Pro Leu Pro Ala Pro Arg Pro Ala Pro Ala Pro Arg Pro Leu Pro
1               5                   10                  15

Glu Pro Leu Pro Ala Pro Arg Pro Ile Pro Ala Pro Leu Pro Arg Pro
                20                  25                  30

Val Pro Ile Val Ser Gln Val Gln Gln Ala Ser Ile Gln Gln Ala Gln
            35                  40                  45

Ser Ser Ser Ala Gln Ser Arg Gln Ser Ala Val Ala Gln Gln Ala Ser
        50                  55                  60

Val Ser Gln Ser Gln Gln Ala Ser Val Ser Gln Ser Gln Gln Ala Ser
65                  70                  75                  80

Val Ser Gln Ser Gln Gln Ala Ser Leu Ser Gln Thr Gln Gln Ala Ser
                85                  90                  95

Val Ser Gln Ser Gln Gln Ser Ser Asn Ala Tyr Ser Ala Ala Ser Asn
            100                 105                 110

Ala Ala Ser Ser Val Ser Gln Ala Ser Ser Ala Ser Ser Tyr Phe Asn
        115                 120                 125

Ser Gln Val Val Gln Ser Thr Leu Ser Ser Ser Leu Gln Ser Ser Ser
    130                 135                 140

Ala Leu Ser Ser Ile Ala Tyr Gly Gln Thr Ser Ala Asn Ile Asn Asp
145                 150                 155                 160

Val Ala Ala Ala Val Ala Arg Ser Val Ser Gln Ser Leu Gly Val Ser
                165                 170                 175

Gln Gln Ala Ala Gln Ser Val Ile Ser Gln Gln Leu Ala Ser Ala Gly
            180                 185                 190

Ala Gly Ala Ser Ala Gln Thr Leu Ala Gln Leu Ile Ser Ser Ala Val
        195                 200                 205

Ser Ser Leu Val Gln Gln Ser Gly Thr Val Ser Ala Gly Gln Glu Gln
    210                 215                 220

Ser Ile Ser Gln Ala Leu Ser Ser Ser Ile Leu Ser Ser Leu Ser Gln
225                 230                 235                 240

Val Val Ala Gln
```

*FIG. 25*

SEQ ID NO: 19

```
Thr Ser Gly Gly Tyr Pro Gly Gly Tyr Pro Gly Gly Gln Gly Ala Gly
1               5                   10                  15

Pro Leu Gly Gly Val Pro Leu Val Ser Gln Ser Leu Asp Asn Leu Gly
            20                  25                  30

Gly Gly Gly Ala Gln Ala Gly Leu Ile Ser Arg Val Ala Asn Ala Leu
            35                  40                  45

Ala Asn Thr Ser Thr Leu Arg Ala Val Leu Arg Arg Gly Val Ser Gln
            50                  55                  60

Asn Thr Val Asn Asn Val Val Gln Arg Thr Val Gln Ser Leu Ala Asn
65                  70                  75                  80

Thr Leu Gly Val Asp Gly Asn Asn Leu Ala Arg Ile Ala Ser Gln Ala
            85                  90                  95

Ile Ser Gln Val Pro Ala Gly Ser Asp Thr Asn Ala Tyr Ala Gln Ala
            100                 105                 110

Leu Ser Thr Ala Leu Val Thr Gly Gly Ile Leu Asn Glu Arg Asn Ile
            115                 120                 125

Asp Ser Leu Gly Ser Arg Val Leu Ser Ala Val Leu Asn Gly Val Ser
            130                 135                 140

Ser Ala Ala Gln Gly Leu Gly Ile Asn Val Asp Thr Gly Asn Leu Gln
145                 150                 155                 160

Gly Asp Ile Arg Ser Ser Thr Gly Phe Leu Ser Thr Gly Ser Ser Ser
            165                 170                 175

Thr Ile Leu Ser Gln Thr Ala Ala Ser Thr Thr Ser Gly Ala Glu Ser
            180                 185                 190
```

FIG. 26

SEQUENCE LISTING

```
<160> NUMBER OF SEQ ID NOS: 39

<210> SEQ ID NO 1
<211> LENGTH: 291
<212> TYPE: DNA
<213> ORGANISM: Nephila clavipes

<400> SEQUENCE: 1
```

| | |
|---|---|
| agccgcctgg cgagcccgga tagcggcgcg cgcgtggcga gcgcggtgag caacctggtg | 60 |
| agcagcggcc cgaccagcag cgcggcgctg agcagcgtga ttagcaacgc ggtgagccag | 120 |
| attggcgcga gcaacccggg cctgagcggc tgcgatgtgc tgattcaggc gctgctggaa | 180 |
| attgtgagcg cgtgcgtgac cattctgagc agcagcagca ttggccaggt gaactatggc | 240 |
| gcggcgagcc agtttgcgca ggtggtgggc cagagcgtgc tgagcgcgtt t | 291 |

<210> SEQ ID NO 2
<211> LENGTH: 1176
<212> TYPE: DNA
<213> ORGANISM: Artificial Sequence
<220> FEATURE:
<223> OTHER INFORMATION: MiSp8

<400> SEQUENCE: 2

| | |
|---|---|
| ggtgccggtg gttatggtcg tggtgctggt gcgggtgccg gtgcagcagc tggtgccggt | 60 |
| gctggcgcag gcggttatgg tggtcagggt ggctacggtg ccggtgccgg tgctggtgcc | 120 |
| gcagccgcag cgggtgcggg tgcaggcggt gctggcggtt atggcagagg tgctggggct | 180 |
| ggtgcaggcg ctgcagccgg tgcgggtgct ggtgcgggtg atatggtgg ccagggtggt | 240 |
| tatggcgctg gcgcaggggc aggcgcagca gcagcagctg ggcaggcgc aggcggtgcc | 300 |
| ggtggctatg gacgcggagc cggtgccggt gcaggggcag cagcgggtgc tggtgccggt | 360 |
| gcagggggtt atggtggcca aggcggatat ggtgcgggtg caggcgctgg tgcagcagca | 420 |
| gccgctggtg ccggtgccgg tggtgcgggt ggctacggaa gaggtgcggg tgccggtgcc | 480 |
| ggtgctgcag cgggtgcggg tgcgggtgcc ggtggttatg gcggtcaggg tgggtatggt | 540 |
| gcgggtgctg gtgcaggcgc agctgcagcc gctggtgctg gtgcaggcgg agccggtgga | 600 |
| tatggccgag gtgctggcgc aggcgctggc gctgctgctg gtgccggtgc gggtgctggg | 660 |
| ggatacggtg gtcaagggg ttatggtgcg ggtgccggtg cgggtgcagc cgcagcagct | 720 |
| ggtgcgggtc gggtggtgc aggggatat ggccgtggtg ccggtgctgg tgcgggtgct | 780 |
| gcagccggtg ctggggcagg ggctggcggt tatgggggtc aaggcggtta tggcgctggt | 840 |
| gctggtgctg gggctgccgc agcagccggt gctggtgctg gcggtgcggg tggttacggt | 900 |
| cggggagctg gcgctggtgc tggcgcagca gcgggtgccg gtgctggtgc cggtggctac | 960 |
| ggtggacaag gtggctatgg tgccggtgca ggcgcagggg ctgcagccgc agccggtgcc | 1020 |
| ggtgccggtg gcgctggggg ttatggtcgc ggagcgggtg caggcgcagg cgcagccgct | 1080 |
| ggcgctggtg cgggtgctgg cggttatggt ggacaagggg gttatggggc tggtgctggc | 1140 |
| gcaggggcag ctgctgcagc gggtgctggc gcttcc | 1176 |

<210> SEQ ID NO 3
<211> LENGTH: 1020
<212> TYPE: DNA
<213> ORGANISM: Artificial Sequence
<220> FEATURE:
<223> OTHER INFORMATION: MaSP18

<400> SEQUENCE: 3

| | |
|---|---|
| ggtgcaggtc aggtggtta tggtggtctg ggtagccagg gtgccggtcg tggtggactg | 60 |
| ggtggtcaag gtgctggtgc agcagcagct gccgcagcag caggcggtgc aggccaaggc | 120 |
| ggatatggcg gactgggttc acagggtgca ggccgtggcg gtttaggtgg tcaaggcgca | 180 |
| ggcgctgctg cagccgcagc ggcagcagct ggccaaggtg gctatggtgg cttaggctca | 240 |

```
cagggtggcg gtgctggaca gggtggatac ggtggccttg gcagtcaagg tgcgggtcgc    300
ggtggtttag gcggtcaggg tgcgggtgcg gctgctgcag ctgcggcagc gggtggtgct    360
gggcaaggcg gttacggtgg attaggtagc caaggtgcag gacgcggagg tcttggtgga    420
cagggtgctg gcgctgctgc ggcagcagca gccgctgggg gtgctggtca agggggttat    480
ggcggtttag gatctcaggg tgcgggacgg ggtggtctgg gagggcaagg ggcaggcgca    540
gcagcagcgg cagctgcagc cggtggtgcc ggacaagggg gatatggggg tcttggctcc    600
caaggcgctg gtcgtggcgg tcttggaggc caaggtgccg gtgccgctgc agcggctgct    660
gctgcagcgg gtcaaggggg atacggtggt ctgggatcac aaggtggtgg cgcagggcaa    720
ggtgggtatg ggggtttagg ttcgcaaggt gctggccgtg ggggactggg aggacagggt    780
gccggtgcgg cagccgctgc agctgctgcg gtggcgctg gtcagggtgg ctatggcgga    840
ttgggctctc aaggggcagg tcggggtggc ttgggaggac aaggtgcggg tgcagccgct    900
gcggcagctg ccgctggcgg agcaggccag ggtggctacg gtggactggg ttcccaaggt    960
gcgggaagag gtggcttggg tggccagggt gcaggggcag cggctgcagc ggcagcagcc   1020

<210> SEQ ID NO 4
<211> LENGTH: 1017
<212> TYPE: DNA
<213> ORGANISM: Artificial Sequence
<220> FEATURE:
<223> OTHER INFORMATION: MaSP28

<400> SEQUENCE: 4
ccgggtcagc agggtccggg tggttatggt cctggccagc agggaccgag cggtccgggt     60
agtgcagcag cagctgcagc agccgcaggc cctggtcagc aaggccctgg tggatatgga    120
ccaggccaac agggtcctgg cggatacggt cctggtcaac aaggtccgtc aggtccgggt    180
tcagccgcag cggctgctgc cgcagcaggt ccaggtggct acggaccggg tcaacaggga    240
cccggtgggt acggaccagg acagcaaggg ccaggcggtt atggccctgg acaacaaggg    300
cctagtggtc ctggttctgc agcggcagcc gctgcggcag ctggtccggg acagcaagga    360
cccggtggat acgtcccggg tcagcaggga cctggcggtt acggaccggg acaacagggt    420
ccatctggtc ctggtagcgc agccgcagca gcagcggctg caggtccagg acaacaaggt    480
cctggtgggt atggtccagg gcagcaaggt ccgagtggtc caggctctgc ggcagcggca    540
gcagcagcag cggacctgg tcaacagggt ccagggggat atgcccagg tcagcaagga    600 ccgggtggct atgggccagg tcaacaaggc cctagcggtc cggatctgc cgcagctgca    660 gcggcagcgg caggtcctgg cggttatgga ccaggtcagc agggtcccgg tggctacggt    720
cccggacaac aaggcccagg gggttacgga cctggccagc aaggtccttc tggaccggga    780
agcgctgcag ccgcagcagc tgcagccggt ccaggccagc aagggcctgg gggttacggt    840
ccgggtcagc aaggcccagg cggatacggt ccaggacaac agggaccaag tggtccggga    900
tcagcagccg ctgccgcagc ggcagccggt cccggtcaac aaggacctgg tggctacggt    960
cctgggcaac agggtcctag cggtccaggg tcagcagcag cagccgcagc tgcagca     1017

<210> SEQ ID NO 5
<211> LENGTH: 1065
<212> TYPE: DNA
<213> ORGANISM: Nephila clavipes

<400> SEQUENCE: 5
aagcttcata tgggatcaac cggtcccggg ggtccgggtg gttatggtcc tggtggtagt     60
```

```
ggtccaggtg gctatggacc gggtggttcc ggtccaggcg gttatggccc tggcggttca    120
ggtccgggtg gatacggacc aggtggcagc ggtccgagtg gtccgggtag tgcagcagca    180
gcagccgcag ctgcaggtcc aggggatat ggtccagggg gtagcggacc tggcggttat     240
gggccaggtg gctctggccc tggtggatat ggcccaggcg gaagtggccc aggtggttac    300
ggacctgggg gatcaggacc aggcggttac ggtccgggtg gctcaggtcc tagcggtccg    360
ggttcagccg cagcggcagc agcagcggca ggaccgggtg gctatgggcc aggggttcg     420 ggacctggtg gttatggacc tggcggaagc ggtcctgggg gttacggtcc aggtggaagt    480
ggaccgtcag gtccaggtag cgcagctgcc gctgcagccg cagcaggtcc aggtgggtac    540
ggtcctggtg gttctggacc gggtgggtat ggtccgggtg gaagcggacc gggtggatat    600
ggccctgggg gatctggtcc tggcggatat ggacctggtg ggtcgggacc aggggggatac   660 ggaccgggtg gtagtggccc aggcggatac ggtcctggcg gtagcggtcc atcaggtccg    720
ggatctgctg ctgctgcggc agctgcagcc ggaccagggg gttatggacc aggtggttca    780
ggaccaggtg gctacggtcc aggcggtagt gggcctgggg gatatggtcc gggtggctct    840
gggcctggcg gttacggacc tggcggtagt ggaccgggtg gttatggccc aggtggctcc    900
ggtccgggtg ggtatgggcc aggtggatct gggccaggcg gttatggtcc aggggggatcg   960 ggtccaggtg gatatggccc aggtggttca ggtccatctg gtccgggttc cgcagctgca   1020
gccgcagccg cagcttccgg agggcccgat atcctcgagg gatcc                   1065

<210> SEQ ID NO 6
<211> LENGTH: 5600
<212> TYPE: DNA
<213> ORGANISM: Artificial Sequence
<220> FEATURE:
<223> OTHER INFORMATION: pET19KT

<400> SEQUENCE: 6
ggccatcatc atcatcatca tcatcatcat cacagcagcg gccatatcga cgacgacgac     60
aagcatatgc tcgaggatcc gggaagcgct agccgcctgg cgagcccgga tagcggcgcg    120
cgcgtggcga gcgcggtgag caacctggtg agcagcggcc cgaccagcag cgcggcgctg    180
agcagcgtga ttagcaacgc ggtgagccag attggcgcga gcaacccggg cctgagcggc    240
tgcgatgtgc tgattcaggc gctgctggaa attgtgagcc gtgcgtgac cattctgagc     300 agcagcagca ttggccaggt gaactatggc gcggcgagcc agtttgcgca ggtggtgggc    360
cagagcgtgc tgagcgcgtt tgctgcttga taagcccgaa aggaagctga gttggctgct    420
gccaccgctg agcaataact agcataaccc cttgggccct ctaaacgggt cttgaggggt    480
tttttgctga aaggaggaac tatatccgga ttggcgaatg ggacgcgccc tgtagcggcg    540
cattaagcgc ggcgggtgtg gtggttacgc gcagcgtgac cgctacactt gccagcgccc    600
tagcgcccgc tcctttcgct ttcttccctt cctttctcgc cacgttcgcc ggctttcccc    660
gtcaagctct aaatcggggg ctcccttag ggttccgatt tagtgcttta cggcacctcg    720
accccaaaaa acttgattag ggtgatggtt cacgtagtgg gccatcgccc tgatagacgg    780 ttttcgccc tttgacgttg gagtccacgt tctttaatag tggactcttg ttccaaactg    840
gaacaacact caaccctatc tcggtctatt cttttgattt ataagggatt ttgccgattt    900
cggcctattg gttaaaaaat gagctgattt aacaaaaatt taacgcgaat tttaacaaaa    960
tattaacgtt tacaatttca ggtggcactt ttcggggaaa tgtgcgcgga acccctattt   1020
```

```
gtttattttt ctaaatacat tcaaatatgt atccgctcat gaattaattc ttagaaaaac    1080
tcatcgagca tcaaatgaaa ctgcaattta ttcatatcag gattatcaat accatatttt    1140
tgaaaaagcc gtttctgtaa tgaaggagaa aactcaccga ggcagttcca taggatggca    1200
agatcctggt atcggtctgc gattccgact cgtccaacat caatacaacc tattaatttc    1260
ccctcgtcaa aaataaggtt atcaagtgag aaatcaccat gagtgacgac tgaatccggt    1320
gagaatggca aaagtttatg catttctttc cagacttgtt caacaggcca gccattacgc    1380
tcgtcatcaa aatcactcgc atcaaccaaa ccgttattca ttcgtgattg cgcctgagcg    1440
agacgaaata cgcgatcgct gttaaaagga caattacaaa caggaatcga atgcaaccgg    1500
cgcaggaaca ctgccagcgc atcaacaata ttttcacctg aatcaggata ttcttctaat    1560
acctggaatg ctgttttccc ggggatcgca gtggtgagta accatgcatc atcaggagta    1620
cggataaaat gcttgatggt cggaagaggc ataaattccg tcagccagtt tagtctgacc    1680
atctcatctg taacatcatt ggcaacgcta cctttgccat gtttcagaaa caactctggc    1740
gcatcgggct tcccatacaa tcgatagatt gtcgcacctg attgcccgac attatcgcga    1800
gcccatttat acccatataa atcagcatcc atgttggaat ttaatcgcgg cctagagcaa    1860
gacgtttccc gttgaatatg gctcataaca cccccttgtat tactgtttat gtaagcagac    1920
agttttattg ttcatgacca aaatccctta acgtgagttt tcgttccact gagcgtcaga    1980
ccccgtagaa aagatcaaag gatcttcttg agatcctttt ttttctgcgcg taatctgctg    2040 cttgcaaaca aaaaaaccac cgctaccagc ggtggtttgt ttgccggatc aagagctacc    2100
aactcttttt ccgaaggtaa ctggcttcag cagagcgcag ataccaaata ctgtccttct    2160
agtgtagccg tagttaggcc accacttcaa gaactctgta gcaccgccta catacctcgc    2220
tctgctaatc ctgttaccag tggctgctgc cagtggcgat aagtcgtgtc ttaccgggtt    2280
ggactcaaga cgatagttac cggataaggc gcagcggtcg ggctgaacgg ggggttcgtg    2340
cacacagccc agcttggagc gaacgaccta caccgaactg agatacctac agcgtgagct    2400
atgagaaagc gccacgcttc ccgaagggag aaaggcggac aggtatccgg taagcggcag    2460
ggtcggaaca ggagagcgca cgagggagct tccaggggga aacgcctggt atctttatag    2520
tcctgtcggg tttcgccacc tctgacttga gcgtcgattt ttgtgatgct cgtcaggggg    2580
gcggagccta tggaaaaacg ccagcaacgc ggccttttta cggttcctgg ccttttgctg    2640
gccttttgct cacatgttct ttcctgcgtt atcccctgat tctgtggata accgtattac    2700
cgcctttgag tgagctgata ccgctcgccg cagccgaacg accgagcgca gcgagtcagt    2760
gagcgaggaa gcggaagagc gcctgatgcg gtattttctc cttacgcatc tgtgcggtat    2820
ttcacaccgc atatatggtg cactctcagt acaatctgct ctgatgccgc atagttaagc    2880
cagtatacac tccgctatcg ctacgtgact gggtcatggc tgcgccccga cacccgccaa    2940
cacccgctga cgcgccctga cgggcttgtc tgctcccggc atccgcttac agacaagctg    3000
tgaccgtctc cgggagctgc atgtgtcaga ggttttcacc gtcatcaccg aaacgcgcga    3060
ggcagctgcg gtaaagctca tcagcgtggt cgtgaagcga ttcacagatg tctgcctgtt    3120
catccgcgtc cagctcgttg agtttctcca gaagcgttaa tgtctggctt ctgataaagc    3180
gggccatgtt aagggcggtt ttttcctgtt tggtcactga tgcctccgtg taagggggat    3240
ttctgttcat gggggtaatg ataccgatga acgagagag atgctcacg atacgggtta    3300 ctgatgatga acatgcccgg ttactggaac gttgtgaggg taaacaactg gcggtatgga    3360
tgcggcggga ccagagaaaa atcactcagg gtcaatgcca gcgcttcgtt aatacagatg    3420
```

```
taggtgttcc acagggtagc cagcagcatc ctgcgatgca gatccggaac ataatggtgc    3480
agggcgctga cttccgcgtt tccagacttt acgaaacacg gaaaccgaag accattcatg    3540
ttgttgctca ggtcgcagac gttttgcagc agcagtcgct tcacgttcgc tcgcgtatcg    3600
gtgattcatt ctgctaacca gtaaggcaac cccgccagcc tagccgggtc ctcaacgaca    3660
ggagcacgat catgcgcacc cgtggccagg acccaacgct gcccgagatg cgccgcgtgc    3720
ggctgctgga gatggcggac gcgatggata tgttctgcca agggttggtt tgcgcattca    3780
cagttctccg caagaattga ttggctccaa ttcttggagt ggtgaatccg ttagcgaggt    3840
gccgccggct tccattcagg tcgaggtggc ccggctccat gcaccgcgac gcaacgcggg    3900
gaggcagaca aggtataggg cggcgcctac aatccatgcc aacccgttcc atgtgctcgc    3960
cgaggcggca taaatcgccg tgacgatcag cggtccagtg atcgaagtta ggctggtaag    4020
agccgcgagc gatccttgaa gctgtccctg atggtcgtca tctacctgcc tggacagcat    4080
ggcctgcaac gcgggcatcc cgatgccgcc ggaagcgaga agaatcataa tggggaaggc    4140
catccagcct cgcgtcgcga acgccagcaa gacgtagccc agcgcgtcgg ccgccatgcc    4200
ggcgataatg gcctgcttct cgccgaaacg tttggtggcg ggaccagtga cgaaggcttg    4260
agcgagggcg tgcaagattc cgaataccgc aagcgacagg ccgatcatcg tcgcgctcca    4320
gcgaaagcgg tcctcgccga aaatgaccca gagcgctgcc ggcacctgtc ctacgagttg    4380
catgataaag aagacagtca taagtgcggc gacgatagtc atgccccgcg cccaccggaa    4440
ggagctgact gggttgaagg ctctcaaggg catcggtcga gatcccggtg cctaatgagt    4500
gagctaactt acattaattg cgttgcgctc actgcccgct ttccagtcgg gaaacctgtc    4560
gtgccagctg cattaatgaa tcggccaacg cgcggggaga ggcggtttgc gtattgggcg    4620
ccagggtggt ttttcttttc accagtgaga cgggcaacag ctgattgccc ttcaccgcct    4680
ggccctgaga gagttgcagc aagcggtcca cgctggtttg ccccagcagg cgaaaatcct    4740
gtttgatggt ggttaacggc gggatataac atgagctgtc ttcggtatcg tcgtatccca    4800
ctaccgagat atccgcacca acgcgcagcc cggactcggt aatggcgcgc attgcgccca    4860
gcgccatctg atcgttggca accagcatcg cagtgggaac gatgccctca ttcagcattt    4920
gcatggtttg ttgaaaaccg gacatggcac tccagtcgcc ttcccgttcc gctatcggct    4980
gaatttgatt gcgagtgaga tatttatgcc agccagccag acgcagacgc gccgagacag    5040
aacttaatgg gcccgctaac agcgcgattt gctggtgacc caatgcgacc agatgctcca    5100
cgcccagtcg cgtaccgtct tcatgggaga aataatact gttgatgggt gtctggtcag    5160
agacatcaag aaataacgcc ggaacattag tgcaggcagc ttccacagca atggcatcct    5220
ggtcatccag cggatagtta atgatcagcc cactgacgcg ttgcgcgaga agattgtgca    5280
ccgccgcttt acaggcttcg acgccgcttc gttctaccat cgacaccacc acgctggcac    5340
ccagttgatc ggcgcgagat ttaatcgccg cgacaatttg cgacggcgcg tgcagggcca    5400
gactggaggt ggcaacgcca atcagcaacg actgtttgcc cgccagttgt tgtgccacgc    5460
ggttgggaat gtaattcagc tccgccatcg ccgcttccac tttttcccgc gttttcgcag    5520
aaacgtggct ggcctggttc accacgcggg aaacggtctg ataagagaca ccggcatact    5580
ctgcgacatc gtataacgtt                                                5600
```

<210> SEQ ID NO 7
<211> LENGTH: 2107
<212> TYPE: DNA

<213> ORGANISM: Artificial Sequence
<220> FEATURE:
<223> OTHER INFORMATION: pET19-SXT

<400> SEQUENCE: 7

```
atccggatat agttcctcct ttcagcaaaa aaccccctcaa gacccgttta gaggccccaa      60
ggggttatgc tagttattcg ctcagcggtg gcagcagcca actcagcttc ctttcgggct     120
tatcaagcag caaacgcgct cagcacgctc tggcccacca cctgcgcaaa ctggctcgcc     180
gcgccatagt tcacctggcc aatgctgctg ctgctcagaa tggtcacgca cgcgctcaca     240
atttccagca gcgcctgaat cagcacatcg cagccgctca ggcccgggtt gctcgcgcca     300
atctggctca ccgcgttgct aatcacgctg ctcagcgccg cgctgctggt cgggccgctg     360
ctcccaggtt gctcaccgcg ctcgccacgc gcgcgccgct atccgggctc gccaggcggc     420
tagcgcttcc cggatcctcg agcatatgct tgtcgtcgtc gtcgatatgg ccgctgctgt     480
gatgatgatg atgatgatga tgatgatggc ccatggtata tctccttctt aaagttaaac     540
aaaattattt ctagagggga attgttatcc gctcacaatt ccctatagt gagtcgtatt      600
aatttcgcgg gatcgagatc tgacctgtta tcgcacaatg attcggttat actgttcgcc     660
gttgtccaac aggaccgcct ataaaggcca aaaattttat tgttagctga gtcaggagat     720
gcggatgtta aagcgtgaaa tgaacattgc cgattatgat gccgaactgt ggcaggctat     780
ggagcaggaa aaagtacgtc aggaagagca catcgaactg atcgcctccg aaaactacac     840
cagcccgcgc gtaatgcagg cgcagggttc tcagctgacc aacaaatatg ctgaaggtta     900
tccgggcaaa cgctactacg gcggttgcga gtatgttgat atcgttgaac aactggcgat     960
cgatcgtgcg aaagaactgt tcggcgctga ctacgctaac gtccagccgc actccggctc    1020
ccaggctaac tttgcggtct acaccgcgct gctggaacca ggtgataccg ttctgggtat    1080
gaacctggcg catggcggtc acctgactca cggttctccg gttaacttct ccggtaaact    1140
gtacaacatc gttccttacg gtatcgatgc taccggtcat atcgactacg ccgatctgga    1200
aaaacaagcc aaagaacaca gccgaaaat gattatcggt ggtttctctg catattccgg    1260
cgtggtggac tgggcgaaaa tgcgtgaaat cgctgacagc atcggtgctt acctgttcgt    1320
tgatatggcg cacgttgcgg gcctggttgc tgctggcgtc tacccgaacc cggttcctca    1380
tgctcacgtt gttactacca ccactcacaa aaccctggcg ggtccgcgcg gcggcctgat    1440
cctggcgaaa ggtggtagcg aagagctgta caaaaactg aactctgccg ttttccctgg    1500
tggtcagggc ggtccgttga tgcacgtaat cgccggtaaa gcggttgctc tgaaagaagc    1560
gatggagcct gagttcaaaa cttaccagca gcaggtcgcg aaaaacgcta aagcgatggt    1620
agaagtgttc ctcgagcgcg gctacaaagt ggtttccggc ggcactgata accacctgtt    1680
cctggttgat ctggttgata aaaacctgac cggtaaagaa gcagacgccg ctctgggccg    1740
tgctaacatc accgtcaaca aaaacagcgt accgaacgat ccgaagagcc cgtttgtgac    1800
ctccggtatt cgcgtgggta ctccggcaat tacgcgtcgc ggcttcaaag aagcagaagc    1860
gaaagaactg gctggctgga tgtgtgacgt gctggacagc atcaatgatg aagccgttat    1920
cgagcgcatc aaaggtaaag ttctcgacat ctgcgcacgt tacccggttt acgcataagc    1980
gaaacggtga tttgctgaca atgtgctcgt tgttcatgtt ggatgcggca tgaacacgtc    2040
gaccgtagcc cgagacgata agttcgctta ccggctcgaa tgaagagagc ttctctcgat    2100
attcagt                                                             2107
```

-continued

<210> SEQ ID NO 8
<211> LENGTH: 97
<212> TYPE: PRT
<213> ORGANISM: Nephila clavipes

<400> SEQUENCE: 8

Ser Arg Leu Ala Ser Pro Asp Ser Gly Ala Arg Val Ala Ser Ala Val
1               5                   10                  15

Ser Asn Leu Val Ser Ser Gly Pro Thr Ser Ala Ala Leu Ser Ser
            20                  25                  30

Val Ile Ser Asn Ala Val Ser Gln Ile Gly Ala Ser Asn Pro Gly Leu
        35                  40                  45

Ser Gly Cys Asp Val Leu Ile Gln Ala Leu Leu Glu Ile Val Ser Ala
    50                  55                  60

Cys Val Thr Ile Leu Ser Ser Ser Ile Gly Gln Val Asn Tyr Gly
65                  70                  75                  80

Ala Ala Ser Gln Phe Ala Gln Val Val Gly Gln Ser Val Leu Ser Ala
                85                  90                  95

Phe

<210> SEQ ID NO 9
<211> LENGTH: 392
<212> TYPE: PRT
<213> ORGANISM: Artificial Sequence
<220> FEATURE:
<223> OTHER INFORMATION: MiSp8

<400> SEQUENCE: 9

Gly Ala Gly Gly Tyr Gly Arg Gly Ala Gly Ala Gly Ala Ala
1               5                   10                  15

Ala Gly Ala Gly Ala Gly Ala Gly Gly Tyr Gly Gly Gln Gly Gly Tyr
            20                  25                  30

Gly Ala Gly Ala Gly Ala Gly Ala Ala Ala Ala Gly Ala Gly Ala
        35                  40                  45

Gly Gly Ala Gly Gly Tyr Gly Arg Gly Ala Gly Ala Gly Ala
    50                  55                  60

Ala Ala Gly Ala Gly Ala Gly Ala Gly Gly Tyr Gly Gly Gln Gly Gly
65                  70                  75                  80

Tyr Gly Ala Gly Ala Gly Ala Gly Ala Ala Ala Ala Gly Ala Gly
                85                  90                  95

Ala Gly Gly Ala Gly Gly Tyr Gly Arg Gly Ala Gly Ala Gly Ala Gly
                100                 105                 110

Ala Ala Ala Gly Ala Gly Ala Gly Ala Gly Gly Tyr Gly Gly Gln Gly
            115                 120                 125

Gly Tyr Gly Ala Gly Ala Gly Ala Gly Ala Ala Ala Ala Gly Ala
    130                 135                 140

Gly Ala Gly Gly Ala Gly Gly Tyr Gly Arg Gly Ala Gly Ala Gly Ala
145                 150                 155                 160

Gly Ala Ala Ala Gly Ala Gly Ala Gly Ala Gly Gly Tyr Gly Gly Gln
                165                 170                 175

Gly Gly Tyr Gly Ala Gly Ala Gly Ala Gly Ala Ala Ala Ala Gly
            180                 185                 190

Ala Gly Ala Gly Gly Ala Gly Gly Tyr Gly Arg Gly Ala Gly Ala Gly
        195                 200                 205

Ala Gly Ala Ala Ala Gly Ala Gly Ala Gly Ala Gly Gly Tyr Gly Gly
    210                 215                 220

Gln Gly Gly Tyr Gly Ala Gly Ala Gly Ala Ala Ala Ala
225                 230                 235                 240

Gly Ala Gly Ala Gly Ala Gly Gly Tyr Gly Arg Gly Ala Gly Ala
            245                 250                 255

Gly Ala Gly Ala Ala Gly Ala Gly Ala Gly Ala Gly Gly Tyr Gly
            260                 265                 270

Gly Gln Gly Gly Tyr Gly Ala Gly Ala Gly Ala Gly Ala Ala Ala
            275                 280                 285

Ala Gly Ala Gly Ala Gly Ala Gly Gly Tyr Gly Arg Gly Ala Gly
            290                 295                 300

Ala Gly Ala Gly Ala Ala Ala Gly Ala Gly Ala Gly Gly Tyr
305                 310                 315                 320

Gly Gly Gln Gly Gly Tyr Gly Ala Gly Ala Gly Ala Ala Ala
            325                 330                 335

Ala Ala Gly Ala Gly Ala Gly Gly Ala Gly Tyr Gly Arg Gly Ala
            340                 345                 350

Gly Ala Gly Ala Gly Ala Ala Gly Ala Gly Ala Gly Ala Gly Gly
            355                 360                 365

Tyr Gly Gly Gln Gly Gly Tyr Gly Ala Gly Ala Gly Ala Gly Ala
            370                 375                 380

Ala Ala Ala Gly Ala Gly Ala Ser
385                 390

<210> SEQ ID NO 10
<211> LENGTH: 340
<212> TYPE: PRT
<213> ORGANISM: Artificial Sequence
<220> FEATURE:
<223> OTHER INFORMATION: MaSP18

<400> SEQUENCE: 10

Gly Ala Gly Gln Gly Gly Tyr Gly Gly Leu Gly Ser Gln Gly Ala Gly
1               5                   10                  15

Arg Gly Gly Leu Gly Gly Gln Gly Ala Gly Ala Ala Ala Ala Ala
            20                  25                  30

Ala Ala Gly Gly Ala Gly Gln Gly Gly Tyr Gly Gly Leu Gly Ser Gln
            35                  40                  45

Gly Ala Gly Arg Gly Gly Leu Gly Gly Gln Gly Ala Gly Ala Ala Ala
        50                  55                  60

Ala Ala Ala Ala Ala Gly Gln Gly Gly Tyr Gly Gly Leu Gly Ser
65                  70                  75                  80

Gln Gly Gly Gly Ala Gly Gln Gly Gly Tyr Gly Gly Leu Gly Ser Gln
            85                  90                  95

Gly Ala Gly Arg Gly Gly Leu Gly Gly Gln Gly Ala Gly Ala Ala Ala
            100                 105                 110

Ala Ala Ala Ala Ala Gly Gly Ala Gly Gln Gly Gly Tyr Gly Gly Leu
        115                 120                 125

Gly Ser Gln Gly Ala Gly Arg Gly Gly Leu Gly Gly Gln Gly Ala Gly
    130                 135                 140

Ala Ala Ala Ala Ala Ala Ala Gly Gly Ala Gly Gln Gly Gly Tyr
145                 150                 155                 160

Gly Gly Leu Gly Ser Gln Gly Ala Gly Arg Gly Gly Leu Gly Gly Gln
            165                 170                 175

Gly Ala Gly Ala Ala Ala Ala Ala Ala Ala Gly Gly Ala Gly Gln
            180                 185                 190

Gly Gly Tyr Gly Gly Leu Gly Ser Gln Gly Ala Gly Gly Leu
            195                 200                 205

Gly Gly Gln Gly Ala Gly Ala Ala Ala Ala Ala Ala Ala Gly
    210                 215                 220

Gln Gly Gly Tyr Gly Gly Leu Gly Ser Gln Gly Gly Ala Gly Gln
225                 230                 235                 240

Gly Gly Tyr Gly Gly Leu Gly Ser Gln Gly Ala Gly Arg Gly Gly Leu
            245                 250                 255

Gly Gly Gln Gly Ala Gly Ala Ala Ala Ala Ala Ala Gly Gly
            260                 265                 270

Ala Gly Gln Gly Gly Tyr Gly Gly Leu Gly Ser Gln Gly Ala Gly Arg
    275                 280                 285

Gly Gly Leu Gly Gly Gln Gly Ala Gly Ala Ala Ala Ala Ala Ala
            290                 295                 300

Ala Gly Gly Ala Gly Gln Gly Gly Tyr Gly Gly Leu Gly Ser Gln Gly
305                 310                 315                 320

Ala Gly Arg Gly Gly Leu Gly Gly Gln Gly Ala Gly Ala Ala Ala
            325                 330                 335

Ala Ala Ala Ala
        340

<210> SEQ ID NO 11
<211> LENGTH: 339
<212> TYPE: PRT
<213> ORGANISM: Artificial Sequence
<220> FEATURE:
<223> OTHER INFORMATION: MaSP28

<400> SEQUENCE: 11

Pro Gly Gln Gln Gly Pro Gly Gly Tyr Gly Pro Gly Gln Gln Gly Pro
1               5                   10                  15

Ser Gly Pro Gly Ser Ala Ala Ala Ala Ala Ala Ala Gly Pro Gly
            20                  25                  30

Gln Gln Gly Pro Gly Gly Tyr Gly Pro Gly Gln Gln Gly Pro Gly Gly
        35                  40                  45

Tyr Gly Pro Gly Gln Gln Gly Pro Ser Gly Pro Gly Ser Ala Ala Ala
    50                  55                  60

Ala Ala Ala Ala Ala Gly Pro Gly Gly Tyr Gly Pro Gly Gln Gln Gly
65                  70                  75                  80

Pro Gly Gly Tyr Gly Pro Gly Gln Gln Gly Pro Gly Gly Tyr Gly Pro
            85                  90                  95

Gly Gln Gln Gly Pro Ser Gly Pro Gly Ser Ala Ala Ala Ala Ala
            100                 105                 110

Ala Ala Gly Pro Gly Gln Gln Gly Pro Gly Gly Tyr Gly Pro Gly Gln
        115                 120                 125

Gln Gly Pro Gly Gly Tyr Gly Pro Gly Gln Gln Gly Pro Ser Gly Pro
    130                 135                 140

Gly Ser Ala Ala Ala Ala Ala Ala Ala Gly Pro Gly Gln Gln Gly
145                 150                 155                 160

Pro Gly Gly Tyr Gly Pro Gly Gln Gln Gly Pro Ser Gly Pro Gly Ser
            165                 170                 175

Ala Ala Ala Ala Ala Ala Ala Gly Pro Gly Gln Gln Gly Pro Gly
            180                 185                 190

Gly Tyr Gly Pro Gly Gln Gln Gly Pro Gly Gly Tyr Gly Pro Gly Gln
        195                 200                 205

Gln Gly Pro Ser Gly Pro Gly Ser Ala Ala Ala Ala Ala Ala
    210             215                 220

Gly Pro Gly Gly Tyr Gly Pro Gly Gln Gln Gly Pro Gly Gly Tyr Gly
225             230                 235                 240

Pro Gly Gln Gln Gly Pro Gly Gly Tyr Gly Pro Gly Gln Gln Gly Pro
                245                 250                 255

Ser Gly Pro Gly Ser Ala Ala Ala Ala Ala Ala Ala Gly Pro Gly
        260                 265                 270

Gln Gln Gly Pro Gly Gly Tyr Gly Pro Gly Gln Gln Gly Pro Gly Gly
            275                 280                 285

Tyr Gly Pro Gly Gln Gln Gly Pro Ser Gly Pro Gly Ser Ala Ala Ala
    290                 295                 300

Ala Ala Ala Ala Ala Gly Pro Gly Gln Gln Gly Pro Gly Gly Tyr Gly
305             310                 315                 320

Pro Gly Gln Gln Gly Pro Ser Gly Pro Gly Ser Ala Ala Ala Ala Ala
            325                 330                 335

Ala Ala Ala

<210> SEQ ID NO 12
<211> LENGTH: 352
<212> TYPE: PRT
<213> ORGANISM: Nephila clavipes

<400> SEQUENCE: 12

Met Gly Ser Thr Gly Pro Gly Gly Pro Gly Gly Tyr Gly Pro Gly Gly
1               5                   10                  15

Ser Gly Pro Gly Gly Tyr Gly Pro Gly Ser Gly Pro Gly Gly Tyr
            20                  25                  30

Gly Pro Gly Gly Ser Gly Pro Gly Gly Tyr Gly Pro Gly Gly Ser Gly
            35                  40                  45

Pro Ser Gly Pro Gly Ser Ala Ala Ala Ala Ala Ala Ala Gly Pro
    50                  55                  60

Gly Gly Tyr Gly Pro Gly Gly Ser Gly Pro Gly Gly Tyr Gly Pro Gly
65              70                  75                  80

Gly Ser Gly Pro Gly Gly Tyr Gly Pro Gly Gly Ser Gly Pro Gly Gly
                85                  90                  95

Tyr Gly Pro Gly Gly Ser Gly Pro Gly Gly Tyr Gly Pro Gly Gly Ser
                100                 105                 110

Gly Pro Ser Gly Pro Gly Ser Ala Ala Ala Ala Ala Ala Ala Gly
            115                 120                 125

Pro Gly Gly Tyr Gly Pro Gly Gly Ser Gly Pro Gly Gly Tyr Gly Pro
130             135                 140

Gly Gly Ser Gly Pro Gly Gly Tyr Gly Pro Gly Gly Ser Gly Pro Ser
145             150                 155                 160

Gly Pro Gly Ser Ala Ala Ala Ala Ala Ala Ala Gly Pro Gly Gly
            165                 170                 175

Tyr Gly Pro Gly Gly Ser Gly Pro Gly Gly Tyr Gly Pro Gly Gly Ser
            180                 185                 190

Gly Pro Gly Gly Tyr Gly Pro Gly Gly Ser Gly Pro Gly Gly Tyr Gly
                195                 200                 205

Pro Gly Gly Ser Gly Pro Gly Gly Tyr Gly Pro Gly Gly Ser Gly Pro
    210                 215                 220

Gly Gly Tyr Gly Pro Gly Gly Ser Gly Pro Ser Gly Pro Gly Ser Ala
225             230                 235                 240

```
Ala Ala Ala Ala Ala Ala Gly Pro Gly Tyr Gly Pro Gly
                245                 250                 255

Ser Gly Pro Gly Gly Tyr Gly Pro Gly Ser Gly Pro Gly Gly Tyr
        260                 265                 270

Gly Pro Gly Gly Ser Gly Pro Gly Gly Tyr Gly Pro Gly Gly Ser Gly
    275                 280                 285

Pro Gly Gly Tyr Gly Pro Gly Gly Ser Gly Pro Gly Gly Tyr Gly Pro
    290                 295                 300

Gly Gly Ser Gly Pro Gly Gly Tyr Gly Pro Gly Gly Ser Gly Pro Gly
305                 310                 315                 320

Gly Tyr Gly Pro Gly Gly Ser Gly Pro Ser Gly Pro Gly Ser Ala Ala
                325                 330                 335

Ala Ala Ala Ala Ala Ser Gly Gly Pro Asp Ile Leu Glu Gly Ser
            340                 345                 350

<210> SEQ ID NO 13
<211> LENGTH: 45
<212> TYPE: PRT
<213> ORGANISM: Nephila clavipes

<400> SEQUENCE: 13

Gly Gly Ala Gly Gln Gly Tyr Gly Gly Gln Gly Ala Gly Gln Gly
1               5                   10                  15

Gly Tyr Gly Gly Leu Gly Ser Gln Gly Ala Gly Arg Gly Gly Leu Gly
            20                  25                  30

Gly Gln Gly Ala Gly Ala Ala Ala Ala Ala Ala Ala
        35                  40                  45

<210> SEQ ID NO 14
<211> LENGTH: 41
<212> TYPE: PRT
<213> ORGANISM: Nephila clavipes

<400> SEQUENCE: 14

Ser Gly Pro Gly Gln Gln Gly Pro Gly Gly Tyr Gly Pro Gly Gln Gln
1               5                   10                  15

Gly Pro Gly Gly Tyr Gly Pro Gly Gln Gln Gly Pro Ser Gly Pro Gly
            20                  25                  30

Ser Ala Ala Ala Ala Ala Ala Ala Ala
        35                  40

<210> SEQ ID NO 15
<211> LENGTH: 55
<212> TYPE: PRT
<213> ORGANISM: Nephila clavipes

<400> SEQUENCE: 15

Gly Ala Gly Ala Gly Gly Ala Gly Gly Tyr Gly Arg Gly Ala Gly Ala
1               5                   10                  15

Gly Ala Gly Ala Ala Ala Gly Ala Gly Ala Ala Ala Gly Ala
            20                  25                  30

Gly Ala Gly Gly Tyr Gly Gly Gln Gly Tyr Gly Ala Gly Ala Gly
        35                  40                  45

Ala Gly Ala Ala Ala Ala Ala
        50                  55

<210> SEQ ID NO 16
<211> LENGTH: 170
<212> TYPE: PRT
```

```
<213> ORGANISM: Artificial Sequence
<220> FEATURE:
<223> OTHER INFORMATION: TuSp

<400> SEQUENCE: 16

Thr Thr Thr Thr Thr Ser Ala Ala Arg Ser Gln Ala Ala Ser Gln Ser
1               5                   10                  15

Ala Ser Ser Ser Tyr Ser Ser Ala Phe Ala Gln Ala Ala Ser Ser Ser
            20                  25                  30

Phe Ala Ile Ser Ser Ala Leu Ser Arg Ala Phe Ser Ser Val Ser Ser
        35                  40                  45

Ala Ser Ala Ala Ser Ser Leu Ala Tyr Ser Ile Gly Leu Ser Ala Ala
    50                  55                  60

Arg Ser Leu Gly Ile Ala Asp Ala Thr Leu Ala Gly Ala Leu Ala Arg
65                  70                  75                  80

Ala Val Gly Ala Leu Gly Gln Gly Ala Thr Ala Ala Ser Tyr Gly Asn
                85                  90                  95

Ala Leu Ser Thr Ala Ala Ala Gln Phe Phe Ala Thr Ala Gly Leu Leu
            100                 105                 110

Asn Ala Gly Asn Ala Ser Ala Leu Ala Ser Ser Phe Ala Arg Ala Phe
        115                 120                 125

Ser Ala Ser Ala Glu Ser Gln Ser Phe Ala Gln Ser Gln Ala Phe Gln
    130                 135                 140

Gln Ala Ser Ala Phe Gln Gln Ala Ala Ser Arg Ser Ala Ser Gln Ser
145                 150                 155                 160

Ala Ala Glu Ala Gly Ser Thr Ser Ser Ser
                165                 170

<210> SEQ ID NO 17
<211> LENGTH: 423
<212> TYPE: PRT
<213> ORGANISM: Artificial Sequence
<220> FEATURE:
<223> OTHER INFORMATION: Flag

<400> SEQUENCE: 17

Ser Gly Ala Gly Gly Ser Gly Pro Gly Gly Ala Gly Pro Gly Gly Val
1               5                   10                  15

Gly Pro Gly Gly Ser Gly Pro Gly Gly Val Gly Pro Gly Gly Ser Gly
            20                  25                  30

Pro Gly Gly Val Gly Pro Gly Gly Ser Gly Pro Gly Gly Val Gly Pro
        35                  40                  45

Gly Gly Ala Gly Gly Pro Tyr Gly Pro Gly Gly Ser Gly Pro Gly Gly
    50                  55                  60

Ala Gly Gly Ala Gly Gly Pro Gly Gly Ala Tyr Gly Pro Gly Gly Ser
65                  70                  75                  80

Tyr Gly Pro Gly Gly Ser Gly Gly Pro Gly Gly Ala Gly Gly Pro Tyr
                85                  90                  95

Gly Pro Gly Gly Glu Gly Pro Gly Gly Ala Gly Gly Pro Tyr Gly Pro
            100                 105                 110

Gly Gly Ala Gly Gly Pro Tyr Gly Pro Gly Gly Ala Gly Gly Pro Tyr
        115                 120                 125

Gly Pro Gly Gly Glu Gly Gly Pro Tyr Gly Pro Gly Gly Ser Tyr Gly
    130                 135                 140

Pro Gly Gly Ala Gly Gly Pro Tyr Gly Pro Gly Gly Pro Tyr Gly Pro
145                 150                 155                 160
```

Gly Gly Glu Gly Pro Gly Gly Ala Gly Gly Pro Tyr Gly Pro Gly Gly
                165                 170                 175

Val Gly Pro Gly Gly Ser Gly Pro Gly Gly Tyr Gly Pro Gly Gly Ser
            180                 185                 190

Gly Pro Gly Gly Tyr Gly Pro Gly Gly Ala Gly Pro Gly Gly Tyr Gly
        195                 200                 205

Pro Gly Gly Ser Gly Pro Gly Gly Tyr Gly Pro Gly Gly Ser Gly Pro
    210                 215                 220

Gly Gly Tyr Gly Pro Gly Gly Ser Gly Pro Gly Gly Tyr Gly Pro Gly
225                 230                 235                 240

Gly Ser Gly Pro Gly Gly Tyr Gly Ser Gly Gly Ala Gly Pro Gly Gly
            245                 250                 255

Tyr Gly Pro Gly Gly Ser Gly Pro Gly Gly Tyr Gly Pro Gly Gly Ser
            260                 265                 270

Gly Pro Gly Gly Tyr Gly Pro Gly Gly Thr Gly Pro Gly Gly Thr Gly
        275                 280                 285

Pro Gly Gly Ser Gly Pro Gly Gly Tyr Gly Pro Gly Gly Ser Gly Pro
    290                 295                 300

Gly Gly Ser Gly Pro Gly Gly Ser Gly Pro Gly Gly Tyr Gly Pro Ser
305                 310                 315                 320

Gly Ser Gly Pro Gly Gly Tyr Gly Pro Ser Gly Ser Gly Pro Gly Gly
            325                 330                 335

Tyr Gly Pro Gly Gly Ser Gly Pro Gly Gly Tyr Gly Pro Gly Gly Ser
            340                 345                 350

Gly Ala Gly Gly Thr Gly Pro Gly Gly Ala Gly Gly Ala Gly Gly Ala
            355                 360                 365

Gly Gly Ser Gly Gly Ala Gly Gly Ser Gly Gly Ala Gly Gly Ser Gly
            370                 375                 380

Gly Ala Gly Gly Ser Gly Gly Val Gly Gly Ser Gly Gly Thr Thr Ile
385                 390                 395                 400

Thr Glu Asp Leu Asp Ile Thr Ile Asp Gly Ala Asp Gly Pro Ile Thr
                405                 410                 415

Ile Ser Glu Glu Leu Thr Ile
            420

<210> SEQ ID NO 18
<211> LENGTH: 244
<212> TYPE: PRT
<213> ORGANISM: Artificial Sequence
<220> FEATURE:
<223> OTHER INFORMATION: PiSP

<400> SEQUENCE: 18

Arg Pro Leu Pro Ala Pro Arg Pro Ala Pro Ala Pro Arg Pro Leu Pro
1               5                   10                  15

Glu Pro Leu Pro Ala Pro Arg Pro Ile Pro Ala Pro Leu Pro Arg Pro
            20                  25                  30

Val Pro Ile Val Ser Gln Val Gln Gln Ala Ser Ile Gln Gln Ala Gln
        35                  40                  45

Ser Ser Ser Ala Gln Ser Arg Gln Ser Ala Val Ala Gln Gln Ala Ser
    50                  55                  60

Val Ser Gln Ser Gln Gln Ala Ser Val Ser Gln Ser Gln Gln Ala Ser
65                  70                  75                  80

Val Ser Gln Ser Gln Gln Ala Ser Leu Ser Gln Thr Gln Gln Ala Ser
            85                  90                  95

```
Val Ser Gln Ser Gln Gln Ser Ser Asn Ala Tyr Ser Ala Ala Ser Asn
            100                 105                 110

Ala Ala Ser Ser Val Ser Gln Ala Ser Ser Ala Ser Tyr Phe Asn
        115                 120                 125

Ser Gln Val Val Gln Ser Thr Leu Ser Ser Leu Gln Ser Ser Ser
    130                 135                 140

Ala Leu Ser Ser Ile Ala Tyr Gly Gln Thr Ser Ala Asn Ile Asn Asp
145                 150                 155                 160

Val Ala Ala Ala Ala Arg Ser Val Ser Gln Ser Leu Gly Val Ser
                165                 170                 175

Gln Gln Ala Ala Gln Ser Val Ile Ser Gln Gln Leu Ala Ser Ala Gly
            180                 185                 190

Ala Gly Ala Ser Ala Gln Thr Leu Ala Gln Leu Ile Ser Ser Ala Val
        195                 200                 205

Ser Ser Leu Val Gln Gln Ser Gly Thr Val Ser Ala Gly Gln Glu Gln
        210                 215                 220

Ser Ile Ser Gln Ala Leu Ser Ser Ile Leu Ser Ser Leu Ser Gln
225                 230                 235                 240

Val Val Ala Gln

<210> SEQ ID NO 19
<211> LENGTH: 192
<212> TYPE: PRT
<213> ORGANISM: Artificial Sequence
<220> FEATURE:
<223> OTHER INFORMATION: AcSp

<400> SEQUENCE: 19

Thr Ser Gly Gly Tyr Pro Gly Gly Tyr Pro Gly Gly Gln Gly Ala Gly
1               5                   10                  15

Pro Leu Gly Gly Val Pro Leu Val Ser Gln Ser Leu Asp Asn Leu Gly
            20                  25                  30

Gly Gly Gly Ala Gln Ala Gly Leu Ile Ser Arg Val Ala Asn Ala Leu
        35                  40                  45

Ala Asn Thr Ser Thr Leu Arg Ala Val Leu Arg Arg Gly Val Ser Gln
50                  55                  60

Asn Thr Val Asn Val Val Gln Arg Thr Val Gln Ser Leu Ala Asn
65                  70                  75                  80

Thr Leu Gly Val Asp Gly Asn Asn Leu Ala Arg Ile Ala Ser Gln Ala
                85                  90                  95

Ile Ser Gln Val Pro Ala Gly Ser Asp Thr Asn Ala Tyr Ala Gln Ala
            100                 105                 110

Leu Ser Thr Ala Leu Val Thr Gly Gly Ile Leu Asn Glu Arg Asn Ile
        115                 120                 125

Asp Ser Leu Gly Ser Arg Val Leu Ser Ala Val Leu Asn Gly Val Ser
130                 135                 140

Ser Ala Ala Gln Gly Leu Gly Ile Asn Val Asp Thr Gly Asn Leu Gln
145                 150                 155                 160

Gly Asp Ile Arg Ser Ser Thr Gly Phe Leu Ser Thr Gly Ser Ser Ser
                165                 170                 175

Thr Ile Leu Ser Gln Thr Ala Ala Ser Thr Thr Ser Gly Ala Glu Ser
            180                 185                 190

<210> SEQ ID NO 20
<211> LENGTH: 45
<212> TYPE: PRT
```

<213> ORGANISM: Artificial Sequence
<220> FEATURE:
<223> OTHER INFORMATION: Artificial Sequence derived from MaSp1 and/or
      MaSp2

<400> SEQUENCE: 20

Gly Gly Ala Gly Gln Gly Gly Tyr Gly Gly Gln Gly Ala Gly Gln Gly
1               5                   10                  15

Gly Tyr Gly Gly Leu Gly Ser Gln Gly Ala Gly Arg Gly Gly Leu Gly
                20                  25                  30

Gly Gln Gly Ala Gly Ala Ala Ala Ala Ala Ala Ala
                35                  40                  45

<210> SEQ ID NO 21
<211> LENGTH: 41
<212> TYPE: PRT
<213> ORGANISM: Artificial Sequence
<220> FEATURE:
<223> OTHER INFORMATION: Artificial Sequence derived from MaSp1 and/or
      MaSp2

<400> SEQUENCE: 21

Ser Gly Pro Gly Gln Gln Gly Pro Gly Tyr Gly Pro Gly Gln Gln
1               5                   10                  15

Gly Pro Gly Gly Tyr Gly Pro Gly Gln Gln Gly Pro Ser Gly Pro Gly
                20                  25                  30

Ser Ala Ala Ala Ala Ala Ala Ala Ala
                35                  40

<210> SEQ ID NO 22
<211> LENGTH: 24
<212> TYPE: PRT
<213> ORGANISM: Artificial Sequence
<220> FEATURE:
<223> OTHER INFORMATION: Artificial Sequence derived from MaSp1 and/or
      MaSp2

<400> SEQUENCE: 22

Gly Gly Ala Gly Gln Gly Gly Tyr Gly Gly Leu Gly Ser Gln Gly Ala
1               5                   10                  15

Gly Arg Gly Gly Leu Gly Gly Gln
                20

<210> SEQ ID NO 23
<211> LENGTH: 32
<212> TYPE: PRT
<213> ORGANISM: Artificial Sequence
<220> FEATURE:
<223> OTHER INFORMATION: Artificial Sequence derived from MaSp1 and/or
      MaSp2

<400> SEQUENCE: 23

Gly Pro Gly Gly Tyr Gly Pro Gly Gln Gln Gly Pro Ser Gly Pro Gly
1               5                   10                  15

Ser Ala Ala Ala Ala Gly Pro Ser Gly Pro Gly Ser Ala Ala Ala Ala
                20                  25                  30

<210> SEQ ID NO 24
<211> LENGTH: 42
<212> TYPE: PRT
<213> ORGANISM: Artificial Sequence
<220> FEATURE:
<223> OTHER INFORMATION: Artificial Sequence derived from MaSp1 and/or
      MaSp2

```
<400> SEQUENCE: 24

Gly Pro Gly Gly Tyr Gly Pro Gly Gln Gln Gly Pro Gly Ser Gln Gly
1               5                   10                  15

Pro Gly Ser Gly Gly Gln Gln Gly Pro Gly Gly Gln Gly Pro Tyr Gly
            20                  25                  30

Pro Ser Ala Ala Ala Ala Ala Ala Ala
            35                  40

<210> SEQ ID NO 25
<211> LENGTH: 62
<212> TYPE: PRT
<213> ORGANISM: Artificial Sequence
<220> FEATURE:
<223> OTHER INFORMATION: Artificial Sequence derived from MaSp1 and/or
      MaSp2
<220> FEATURE:
<221> NAME/KEY: misc_feature
<222> LOCATION: (47)..(47)
<223> OTHER INFORMATION: Xaa can be any naturally occurring amino acid

<400> SEQUENCE: 25

Pro Gly Gly Gly Gly Ala Gly Gln Gly Gly Tyr Gly Gly Leu Gly Ser
1               5                   10                  15

Gln Gly Ala Gly Arg Gly Gly Leu Gly Gly Gln Gly Ala Gly Ala Ala
            20                  25                  30

Ala Ala Ala Ala Gly Pro Gly Gly Tyr Gly Pro Gly Gln Gln Xaa Gly
            35                  40                  45

Pro Ser Gly Pro Gly Ser Ala Ala Ala Ala Ala Ala Ala Ala
    50                  55                  60

<210> SEQ ID NO 26
<211> LENGTH: 20
<212> TYPE: PRT
<213> ORGANISM: Artificial Sequence
<220> FEATURE:
<223> OTHER INFORMATION: Artificial Sequence derived from MaSp2 and/or
      flagelliform

<400> SEQUENCE: 26

Gly Pro Gly Gly Ala Gly Pro Gly Gly Ala Gly Pro Gly Gly Ala Gly
1               5                   10                  15

Pro Gly Gly Ala
            20

<210> SEQ ID NO 27
<211> LENGTH: 35
<212> TYPE: PRT
<213> ORGANISM: Artificial Sequence
<220> FEATURE:
<223> OTHER INFORMATION: Artificial Sequence derived from MaSp2 and/or
      flagelliform

<400> SEQUENCE: 27

Gly Pro Gly Gly Ala Gly Pro Gly Gly Ala Gly Pro Gly Gly Ala Gly
1               5                   10                  15

Pro Gly Gly Ala Gly Pro Ser Gly Pro Gly Ser Ala Ala Ala Ala Ala
            20                  25                  30

Ala Ala Ala
        35

<210> SEQ ID NO 28
<211> LENGTH: 35
<212> TYPE: PRT
```

-continued

```
<213> ORGANISM: Artificial Sequence
<220> FEATURE:
<223> OTHER INFORMATION: Artificial Sequence derived from MaSp2 and/or
      flagelliform

<400> SEQUENCE: 28

Gly Pro Gly Gly Tyr Gly Pro Gly Gly Ser Gly Pro Gly Gly Tyr Gly
1               5                   10                  15

Pro Gly Gly Ser Gly Pro Ser Gly Pro Gly Ser Ala Ala Ala Ala Ala
            20                  25                  30

Ala Ala Ala
        35

<210> SEQ ID NO 29
<211> LENGTH: 21
<212> TYPE: PRT
<213> ORGANISM: Artificial Sequence
<220> FEATURE:
<223> OTHER INFORMATION: Artificial Sequence derived from MaSp2 and/or
      flagelliform

<400> SEQUENCE: 29

Gly Gly Ala Gly Gly Ser Gly Gly Ala Gly Gly Ser Gly Gly Val Gly
1               5                   10                  15

Gly Ser Gly Gly Thr
            20

<210> SEQ ID NO 30
<211> LENGTH: 101
<212> TYPE: PRT
<213> ORGANISM: Artificial Sequence
<220> FEATURE:
<223> OTHER INFORMATION: Artificial Sequence derived from MaSp2 and/or
      flagelliform

<400> SEQUENCE: 30

Gly Gly Ala Gly Gly Ser Gly Gly Ala Gly Gly Ser Gly Gly Val Gly
1               5                   10                  15

Gly Ser Gly Gly Thr Gly Pro Gly Gly Ser Pro Gly Gly Tyr Gly
            20                  25                  30

Pro Gly Gly Ser Gly Pro Gly Gly Tyr Gly Pro Gly Gly Ser Gly Pro
            35                  40                  45

Gly Gly Tyr Gly Pro Gly Gly Ser Gly Pro Gly Gly Tyr Gly Pro Gly
        50                  55                  60

Gly Ser Gly Pro Gly Gly Tyr Gly Pro Gly Gly Ser Gly Pro Gly Gly
65                  70                  75                  80

Tyr Gly Pro Gly Gly Ser Gly Pro Gly Gly Tyr Gly Pro Gly Gly Ser
                85                  90                  95

Gly Pro Gly Gly Tyr
            100

<210> SEQ ID NO 31
<211> LENGTH: 51
<212> TYPE: PRT
<213> ORGANISM: Artificial Sequence
<220> FEATURE:
<223> OTHER INFORMATION: Artificial Sequence derived from MaSp2 and/or
      flagelliform

<400> SEQUENCE: 31

Gly Gly Ala Gly Gly Ser Gly Gly Ala Gly Gly Ser Gly Gly Val Gly
1               5                   10                  15
```

```
Gly Ser Gly Gly Thr Thr Ile Glu Asp Leu Asp Ile Thr Ile Asp Gly
            20                  25                  30

Ala Asp Gly Pro Ile Thr Ile Ser Glu Glu Leu Thr Ile Ser Gly Ala
            35                  40                  45

Gly Gly Ser
    50

<210> SEQ ID NO 32
<211> LENGTH: 132
<212> TYPE: PRT
<213> ORGANISM: Artificial Sequence
<220> FEATURE:
<223> OTHER INFORMATION: Artificial Sequence derived from MaSp2 and/or
      flagelliform

<400> SEQUENCE: 32

Gly Gly Ala Gly Gly Ser Gly Gly Ala Gly Gly Ser Gly Gly Val Gly
1               5                   10                  15

Gly Ser Gly Gly Thr Gly Pro Gly Gly Ser Gly Pro Gly Gly Tyr Gly
            20                  25                  30

Pro Gly Gly Ser Gly Pro Gly Gly Tyr Gly Pro Gly Gly Ser Gly Pro
            35                  40                  45

Gly Gly Tyr Gly Pro Gly Gly Ser Gly Pro Gly Gly Tyr Gly Pro Gly
        50                  55                  60

Gly Ser Gly Pro Gly Gly Tyr Gly Pro Gly Gly Ser Gly Pro Gly Gly
65                  70                  75                  80

Tyr Gly Pro Gly Gly Ser Gly Pro Gly Gly Tyr Gly Pro Gly Gly Ser
                85                  90                  95

Gly Pro Gly Gly Tyr Thr Thr Ile Glu Asp Leu Asp Ile Thr Ile Asp
            100                 105                 110

Gly Ala Asp Gly Pro Ile Thr Ile Ser Glu Glu Leu Thr Ile Ser Gly
            115                 120                 125

Ala Gly Gly Ser
    130

<210> SEQ ID NO 33
<211> LENGTH: 144
<212> TYPE: PRT
<213> ORGANISM: Artificial Sequence
<220> FEATURE:
<223> OTHER INFORMATION: Artificial Sequence derived from MaSp2 and/or
      flagelliform

<400> SEQUENCE: 33

Gly Gly Ala Gly Gly Ser Gly Gly Ala Gly Gly Ser Gly Gly Val Gly
1               5                   10                  15

Gly Ser Gly Gly Thr Gly Pro Gly Gly Ser Gly Pro Gly Gly Tyr Gly
            20                  25                  30

Pro Gly Gly Ser Gly Pro Gly Gly Tyr Gly Pro Gly Gly Ser Gly Pro
            35                  40                  45

Gly Gly Tyr Gly Pro Gly Gly Ser Gly Pro Gly Gly Tyr Gly Pro Gly
        50                  55                  60

Gly Ser Gly Pro Gly Gly Tyr Gly Pro Gly Gly Ser Gly Pro Gly Gly
65                  70                  75                  80

Tyr Gly Pro Gly Gly Ser Gly Pro Gly Gly Tyr Gly Pro Gly Gly Ser
                85                  90                  95

Gly Pro Gly Gly Tyr Thr Thr Ile Glu Asp Leu Asp Ile Thr Ile Asp
            100                 105                 110
```

-continued

Gly Ala Asp Gly Pro Ile Thr Ile Ser Glu Glu Leu Thr Ile Ser Gly
        115                 120                 125

Ala Gly Gly Ser Gly Pro Gly Gly Pro Ala Ala Ala Ala Ala Ala
    130                 135                 140

<210> SEQ ID NO 34
<211> LENGTH: 31
<212> TYPE: PRT
<213> ORGANISM: Artificial Sequence
<220> FEATURE:
<223> OTHER INFORMATION: Peptide H

<400> SEQUENCE: 34

Thr Ile Ile Glu Asp Leu Asp Ile Thr Ile Asp Gly Ala Asp Gly Pro
1               5                   10                  15

Ile Thr Ile Ser Glu Glu Leu Thr Ile Ser Gly Ala Gly Gly Ser
            20                  25                  30

<210> SEQ ID NO 35
<211> LENGTH: 8
<212> TYPE: PRT
<213> ORGANISM: Artificial Sequence
<220> FEATURE:
<223> OTHER INFORMATION: Peptide F

<400> SEQUENCE: 35

Gln Gln Ser Ser Val Ala Gln Ser
1               5

<210> SEQ ID NO 36
<211> LENGTH: 29
<212> TYPE: PRT
<213> ORGANISM: Artificial Sequence
<220> FEATURE:
<223> OTHER INFORMATION: Peptide G

<400> SEQUENCE: 36

Arg Pro Leu Pro Ala Pro Arg Pro Leu Pro Ala Pro Leu Pro Ala Pro
1               5                   10                  15

Arg Pro Ile Pro Ala Pro Leu Pro Arg Pro Val Pro Ile
            20                  25

<210> SEQ ID NO 37
<211> LENGTH: 10
<212> TYPE: PRT
<213> ORGANISM: Nephila clavipes

<400> SEQUENCE: 37

Gly Pro Gly Gly Ser Gly Pro Gly Gly Tyr
1               5                   10

<210> SEQ ID NO 38
<211> LENGTH: 16
<212> TYPE: PRT
<213> ORGANISM: Nephila clavipes

<400> SEQUENCE: 38

Gly Gly Pro Ser Gly Pro Gly Ser Ala Ala Ala Ala Ala Ala Ala Ala
1               5                   10                  15

<210> SEQ ID NO 39
<211> LENGTH: 20
<212> TYPE: PRT
<213> ORGANISM: Artificial Sequence
<220> FEATURE:

```
<223> OTHER INFORMATION: Artificial Sequence derived from MaSp2 and/or
      flagelliform

<400> SEQUENCE: 39

Gly Pro Gly Gly Tyr Gly Pro Gly Gly Ser Gly Pro Gly Gly Tyr Gly
1               5                   10                  15

Pro Gly Gly Ser
            20
```

EXPRESSION SYSTEMS AND ASSOCIATED METHODS

RELATED APPLICATIONS

This application claims the benefit under 35 U.S.C. §119(e) of U.S. Provisional Patent Application No. 62/061,574, filed Oct. 8, 2014, and titled "EXPRESSION SYSTEMS AND ASSOCIATED METHODS," which is incorporated, in its entirety, by this reference.

The following applications and patents are related and are hereby incorporated by reference in their entirety: U.S. Provisional Application Nos. 61/917,259 and 61/977,552; U.S. application Ser. Nos. 14/042,183; 14/459,244; and U.S. Pat. Nos. 7,521,228; 7,723,109; 7,288,391; 7,157,615; 5,989,894; 5,728,810; 5,733,771; 5,756,677; and 5,994,099.

GOVERNMENT SPONSORED RESEARCH

This invention was made, at least in part, with government support under contract number W911NF-14-1-0267, awarded by the Department of Defense, and contract number IIP-1318194, awarded by the National Science Foundation. The government has certain rights in the invention.

TECHNICAL FIELD

The present disclosure relates to expression systems and associated methods for enhancing the production of recombinant proteins. More specifically, it relates to spider silk protein expression system and methods of the same.

BACKGROUND

Spider silk is a natural protein fiber produced by the spiders. Despite being a biopolymer, spider silk's tensile strength is comparable to that of high-grade alloy steel, but it has only about a sixth of the density of steel. Spider silk has been used by humans for many, many years. The ancient Greeks used it to stop wounds from bleeding. Optical targeting devices and fishnets are more recent applications of spider silks. The current study of spider silk opens the potential use of spider silks in strong and biodegradable materials such as wear-resistant lightweight clothing, rust-free panels on cars, and some biomedical devices.

Because spiders are hard to farm like silkworms in high densities because of their carnivorous nature, it is difficult to produce large amount of spider silks from farm-raised spiders. Genetic engineering is an alternative approach to produce large quantities of spider silk for commercial applications. The relevant genes of spiders have been cloned and inserted into several different organisms, such as *E. coli*, alfalfa, goat and silkworm, to make spider silks by different groups. Producing large-scale truly spider-like silk, however, remains a big challenge due to the small protein size, low yield and low water solubility of bio-synthetic spider silk.

BRIEF SUMMARY

In one embodiment, what is disclosed is a method of producing a synthetic spider silk. The method includes transforming one or more bacterial cells with an expression vector system comprising a first antibiotic resistance gene, a spider silk protein-encoding open reading frame, and a transfer RNA gene, to generate transformed bacterial cells. The method also includes fermenting the transformed bacterial cells in a culture medium. The method includes inducing spider silk protein expression in the cultured *E. coli* with an inducer. The method includes purifying the synthetic spider silk protein.

In another embodiment, described herein is a DNA vector system for expressing spider silk proteins in bacteria. The vector system includes a first antibiotic resistance gene, a spider silk protein-encoding open reading frame, and a transfer RNA gene.

In one aspect, a method of producing a synthetic spider silk is disclosed. The method includes transforming one or more bacterial cells with an expression vector system comprising a first antibiotic resistance gene, a spider silk protein-encoding open reading frame, and a transfer RNA gene, to generate transformed bacterial cells; fermenting the transformed bacterial cells in a culture medium; inducing spider silk protein expression in the cultured *E. coli* with an inducer, and purifying the synthetic spider silk protein.

In one embodiment, the expression vector system consists of a single vector. In one embodiment, the expression vector system includes more than one type of vector, where the first antibiotic resistance gene and the spider silk protein-encoding open reading frame residing on a first vector, and the transfer RNA gene and a second resistance gene to a second antibiotic residing on a second vector.

In one embodiment, the spider silk protein-encoding open reading frame encodes at least one of flagelliform silk, MaSp 1, MaSp2, MiSp, or a combination thereof.

In one embodiment, the protein-encoding open reading frame includes sequence coding for a C-terminal tail.

In one embodiment, the step of inducing spider silk protein expression includes holding the fermentation temperature within a temperature range of from about 20° C. to about 25° C.

In one embodiment, the inducer is selected from the group consisting of isopropyl β-D-1-thiogalactopyranoside, lactose, maltose, rhamnose, and another sugar-based induction system.

In one embodiment, the inducer is a heat shock step. In one embodiment, the step of inducing spider silk protein expression includes simultaneously adding the inducer and an antibiotic to which the first antibiotic resistance gene provides resistance.

In one embodiment, the antibiotic is an aminoglycoside antibiotic. In one embodiment, the aminoglycoside antibiotic is selected from the group consisting of: a kanamycin, a neomycin, streptomycin, amikacin, tobramycin, dibekacin, gentamycin, sisomicin, and netilmicin. In one embodiment, the aminoglycoside antibiotic is kanamycin.

In one embodiment, the method includes monitoring a level of glucose in the culture medium and supplementing the culture medium with glucose and an antibiotic when the glucose level falls below a predetermined threshold amount.

In one embodiment, the method includes monitoring a pH of the culture medium and adjusting the pH of the culture medium with a nitrogen-containing base when the pH falls below a predetermined threshold amount. In one embodiment, the nitrogen-containing base is ammonium hydroxide.

In another aspect, a DNA vector system for expressing spider silk proteins in bacteria is disclosed. The system includes a first antibiotic resistance gene, a spider silk protein-encoding open reading frame, and a transfer RNA gene.

In some embodiments, the spider silk protein-encoding open reading frame encodes for at least one of flagelliform silk, MaSp 1, MaSp2, MiSp, or a combination thereof.

In some embodiments, the transfer RNA gene encodes for a glycine-bearing transfer RNA.

In some embodiments, all of (i) the resistance gene to the first antibiotic, (ii) the spider silk protein-encoding open reading frame, and (iii) a transfer RNA gene reside on a single DNA vector.

In some embodiments, the resistance gene to the first antibiotic and the spider silk protein-encoding open reading frame reside on a first vector, and the transfer RNA gene resides on a second vector with a resistance gene to a second antibiotic.

BRIEF DESCRIPTION OF THE DRAWINGS

FIG. 8 is a nucleotide sequence corresponding to SEQ ID NO: 1 of the present disclosure;

FIG. 9 is a nucleotide sequence corresponding to SEQ ID NO: 2 of the present disclosure;

FIG. 10 is a nucleotide sequence corresponding to SEQ ID NO: 3 of the present disclosure;

FIG. 11 is a nucleotide sequence corresponding to SEQ ID NO: 4 of the present disclosure;

FIG. 12 is a nucleotide sequence corresponding to SEQ ID NO: 5 of the present disclosure;

FIG. 13 is nucleotide sequences corresponding to SEQ ID NO: 6 of the present disclosure;

FIG. 14 is a nucleotide sequence corresponding to SEQ ID NO: 7 of the present disclosure;

FIG. 15 is an amino acid sequence corresponding to SEQ ID NO: 8 of the present disclosure;

FIG. 16 is an amino acid sequence corresponding to SEQ ID NO: 9 of the present disclosure;

FIG. 17 is an amino acid sequence corresponding to SEQ ID NO: 10 of the present disclosure;

FIG. 18 is an amino acid sequence corresponding to SEQ ID NO: 11 of the present disclosure;

FIG. 19 is an amino acid sequence corresponding to SEQ ID NO: 12 of the present disclosure;

FIG. 20 is an amino acid sequence corresponding to SEQ ID NO: 13 of the present disclosure;

FIG. 21 is an amino acid sequence corresponding to SEQ ID NO: 14 of the present disclosure;

FIG. 22 is an amino acid sequence corresponding to SEQ ID NO: 15 of the present disclosure;

FIG. 23 is an amino acid sequence corresponding to SEQ ID NO: 16 of the present disclosure;

FIG. 24 is an amino acid sequence corresponding to SEQ ID NO: 17 of the present disclosure;

FIG. 25 is an amino acid sequence corresponding to SEQ ID NO: 18 of the present disclosure; and FIG. 26 is an amino acid sequence corresponding to SEQ ID NO: 19 of the present disclosure.

DETAILED DESCRIPTION

Figure 1:
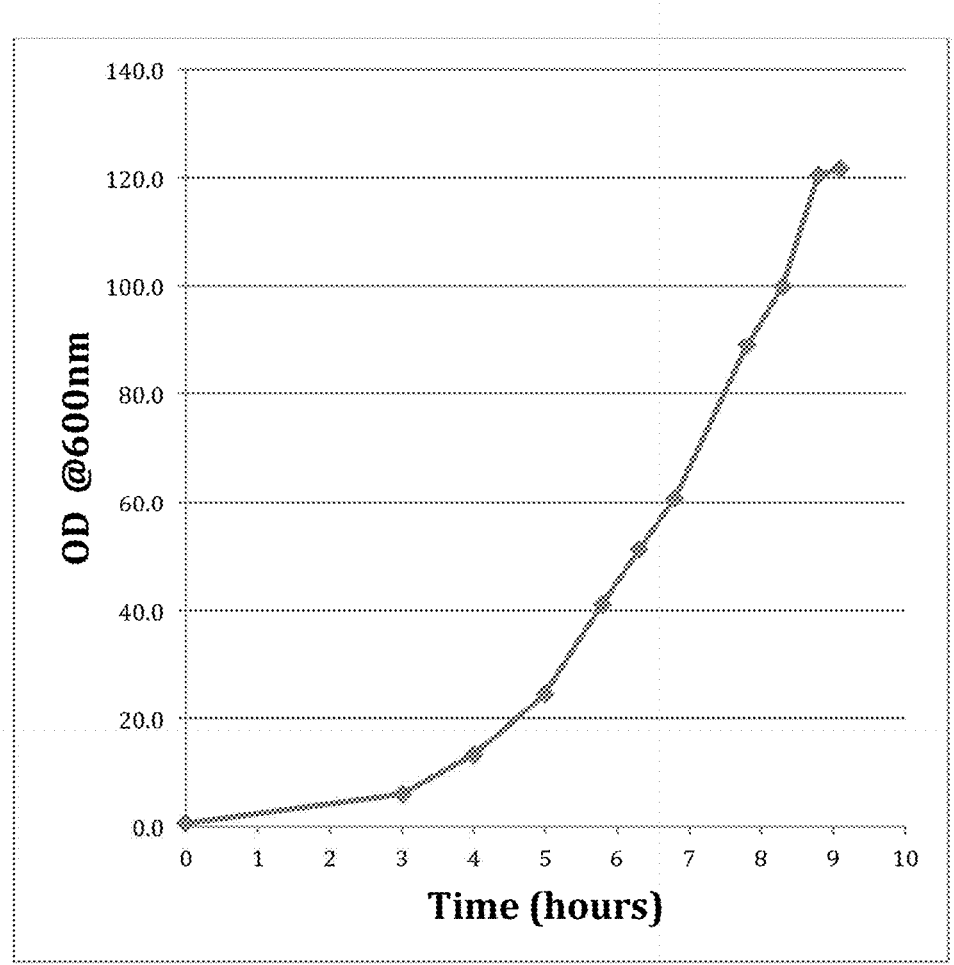
FIG. 1 is a vector map in accordance with an embodiment of the present disclosure.

The present disclosure relates to apparatuses, systems, and associated methods for the expression of spider silk proteins in E. coli. In the following description, numerous specific details are provided for a thorough understanding of specific preferred embodiments. Those skilled in the art, however, will recognize that embodiments can be practiced without one or more of the specific details, or with other methods, components, materials, etc. In some cases, well-known structures, materials, or operations are not shown or described in detail in order to avoid obscuring aspects of the preferred embodiments. Furthermore, the described features, structures, or characteristics may be combined in any suitable manner in a variety of alternative embodiments. Thus, the following more detailed description of the embodiments of the present invention, as illustrated in some aspects in the drawings, is not intended to limit the scope of the invention, but is merely representative of the various embodiments of the invention.

In this specification and the claims that follow, singular forms such as "a," "an," and "the" include plural forms unless the content clearly dictates otherwise. All ranges disclosed herein include, unless specifically indicated, all endpoints and intermediate values. In addition, "optional" or "optionally" refer, for example, to instances in which subsequently described circumstance may or may not occur, and include instances in which the circumstance occurs and instances in which the circumstance does not occur. The terms "one or more" and "at least one" refer, for example, to instances in which one of the subsequently described circumstances occurs, and to instances in which more than one of the subsequently described circumstances occurs.

The present disclosure covers methods, compositions, reagents, and kits for the expression of spider silk proteins. Particularly, described herein are DNA vectors and protein expression protocols for bio-synthetic production of spider silk protein by bacteria, in one embodiment E. coli. A plasmid vector system is also described that drives greatly increased expression of a spider silk protein gene to a level which exceeds other expression systems by unexpectedly high amounts, in one embodiment based on those from the golden orb weaving spider Nephila clavipes. Media conditions, fermentation parameters, and specific protein induction steps are disclosed herein. The result is a fermentation process which can express spider silk proteins in E. coli at a level at or above 0.5 g/L.

E. coli strains suitable for transformation by DNA vectors and expression of protein constructs in accordance with principles of the present invention may include BL21 Star™ (DE3) chemically competent E. coli (Life Technologies, Carlsbad, Calif., USA).

Expression vector systems can be generated by modification of a commercially available protein expression vector containing a bacterial origin of replication, such as a pET-family vector, particularly pET19b vector. Expression in pET family vectors is generally driven by the T7 promoter, but other promoters may be employed too. The expression vector may consist of a single vector, or may be made up of multiple DNA vectors, that are either transformed simultaneously into the *E. coli* cells, or transformed in stepwise fashion as needed.

In the one vector system, the vector may be a pET19b vector in which the ampicillin resistance gene has been replaced with an aminoglycoside resistance gene, specifically a kanamycin resistance gene, even more specifically a kanamycin resistance gene from a pET26b vector. As will be explained below, use of an aminoglycoside antibacterial compound provides a result with surprisingly high expression of spider silk proteins in fermentation expression systems.

In order to increase expression levels of recombinant spider silk proteins that are rich in glycine or proline, genes for expression of higher levels of transfer RNA (tRNA), which become charged with these amino acids, are incorporated into the vector system. These tRNAs can have anticodons to any combination of the glycine codons GGU, GGC, GGA, and GGG, and proline codons CCU, CCA, CCC, CCG. The glycine-bearing and/or proline-bearing tRNA genes may reside on the same DNA molecule as the reading frame for expression of the spider silk construct, or may be provided on a second vector. If provided on a second vector, the tRNA genes are co-resident with a second, different antibiotic resistance gene.

The vector system may also incorporate a gene that results in the expression of serine hydroxyl methyl transferase (SHMT), which converts the amino acid serine to glycine. The SHMT expression gene may reside on any vector of a vector system. A vector including SHMT and tRNA expression genes is termed pET-SX. In one embodiment, pET-SX provides an aminoglycoside resistance gene. In one embodiment, the vector system provides only the SHMT gene. In another embodiment, the vector system provides tRNA genes but not the SHMT gene. In another embodiment, the vector system provides both the SHMT gene and tRNA expression genes.

In one embodiment, a two-vector system may be employed, with the spider silk expression gene on a first vector, and tRNA expression genes on a second vector. Such an arrangement allows for transformation with smaller vectors, which increases ease of handling and transformation, and may be accompanied by an increase in protein expression. In one embodiment, the first vector may provide resistance to an aminoglycoside compound, including but not limited to a kanamycin, a neomycin, streptomycin, amikacin, tobramycin, dibekacin, gentamycin, sisomicin, and netilmicin, while the second vector has a resistance gene against another antibiotic, such as chloramphenicol.

Silk modules to be overexpressed are cloned into at least one vector of the vector system. In one embodiment, a 1.1 kbp monomer gene may be synthesized, for instance by GeneArt® (Life Technologies, Carlsbad, Calif.), to contain the consensus motif of naturally occurring highly repetitive spider silk-like sequences from the golden orb weaving spider *Nephila clavipes*. Since the protein sequences of the orb weaving spiders are highly conserved the technology described here will work for all of them. The complete monomer sequence (FlYS, SEQ ID NO: 12) includes the coding sequences for flagelliform silk-like putative elastic motif, GPGGSGPGGY (FlY) (SEQ ID NO: 37) combined with the major ampullate 2 silk-like putative strength motif, linker-polyalanine—GGPSGPGSA$_8$ (S) (SEQ ID NO: 38). Multimers (FlYS)$_n$ were generated by recombinant DNA technology using a compatible but non-regenerable cloning strategy, that is, by cloning using overhangs which may or may not be generated by restriction digestion, in such a way that the restriction sites are destroyed after ligation. Cloning of the trimer (FlYS)$_3$~3,300 bp was confirmed by partially sequencing using vector specific primers. Other constructs that were cloned for expression in this way are MaSp 1, MaSp2, FlAS and MiSp. The (FlYS)$_3$ construct cloned into pET-SX based on pET19 and having an aminoglycoside resistance gene (or kanamycin resistance gene) is referred to as pET19K-SX-FlYS$_3$.

With regard to the sequences of constructs, a variety of different motifs are contemplated. In some cases, one silk motif, as in for example FlYS$_1$, encoded by SEQ ID NO. 5, will be employed. Other constructs may include two, three, four, five, six, seven, eight, nine, ten, eleven, twelve, or more silk motif repeats. Although natural spider silk proteins may be larger (for instance, in the 250-500 kilodalton range), smaller constructs may be employed as they are a more manageable size and may have better expression than wild type constructs.

Certain spider silk protein sequences contain not only the repeating motifs (such as FlY and FlYS described above) but also a non-repeating C-terminal tail. The C-terminal tail is encoded by SEQ ID NO: 1 and increases the size of a construct but may also increase ease of spinning silk fibers after the protein has been purified. It is envisioned that any spider silk sequence, including those described above, falls within the scope of this invention, with or without the presence of a C-terminal tail in the construct.

A variety of silk proteins can be used in the vectors described herein. Such proteins may include sequences conventionally known for silk proteins (see for example, U.S. Pat. No. 7,288,391, incorporated herein by reference in its entirety).

Constructs whose coding sequences may be incorporated into vectors of the present disclosure, and which may be expressed by a fermentation process as described herein, include those identified in U.S. patent application No. 61/707,571; Ser. No. 14/042,183; PCT/US2013/062722; 61/865,487; and 61/917,259 that are incorporated herein by reference in their entirety. Constructs suitable for inclusion in vectors and production by a fermentation protocol include but are not limited to: major ampullate, minor ampullate, flagelliform, tubuliform, aggregate, aciniform and pyriform proteins. These proteins may be any type of biofilament proteins such as those produced by a variety of arachnids including, for example, *Nephila clavipes, Araneus* ssp. and *A. diadematus*. Also suitable for use in the invention are proteins produced by insects such as *Bombyx mori*. Dragline silk produced by the major ampullate gland of *Nephila clavipes* occurs naturally as a mixture of at least two proteins, designated as MaSpI and MaSpII. Similarly, dragline silk produced by *A. diadematus* is also composed of a mixture of two proteins, designated ADF-3 and ADF-4.

The spider silk proteins may be monomeric proteins, fragments thereof, or dimers, trimers, tetramers or other multimers of a monomeric protein. The proteins are encoded by nucleic acids, which can be joined to a variety of expression control elements, including tissue-specific animal or plant promotors, enhancers, secretory signal sequences and terminators. These expression control sequences, in addition to being adaptable to the expression of a variety of gene products, afford a level of control over the timing and extent of production.

Spider silk proteins are designated according to the gland or organ of the spider in which they are produced. Spider silks known to exist include major ampullate (MaSp1, SEQ ID NO. 13, and MaSp2. SEQ ID NO: 14), minor ampullate (MiSp, SEQ ID NO: 15), flagelliform (Flag, SEQ ID NO: 17), tubuliform (SEQ ID NO: 16), aggregate, aciniform (SEQ ID NO: 19), and pyriform (SEQ ID NO: 18) spider silk proteins. Peptides including eight repeats of MaSp1 (SEQ ID NO: 10), MaSp2 (SEQ ID NO: 11), and MiSp (SEQ ID NO: 9), are artificial sequences which can also be used.

Spider silk proteins derived from each organ are generally distinguishable from those derived from other synthetic organs by virtue of their physical and chemical properties. For example, major ampullate silk, or dragline silk, is extremely tough. Minor ampullate silk, used in web construction, has high tensile strength. An orb-web's capture spiral, in part composed of flagelliform silk, is elastic and can triple in length before breaking. Tubuliform silk is used in the outer layers of egg-sacs, whereas aciniform silk is involved in wrapping prey and pyriform silk is laid down as the attachment disk.

Sequencing of spider silk proteins has revealed that these proteins are dominated by iterations of four simple amino acid motifs: (1) polyalanine (Alan); (2) alternating glycine and alanine (GlyAla)$_n$; (3) GlyGlyXaa; and (4) GlyProGly (Xaa)$_n$, where Xaa represents a small subset of amino acids, including Ala, Tyr, Leu and Gln (for example, in the case of the GlyProGlyXaaXaa motif, GlyProGlyGlnGln is the major form). Spider silk proteins may also contain spacers or linker regions comprising charged groups or other motifs, which separate the iterated peptide motifs into clusters or modules.

In some embodiments, suitable spider silk proteins that can be used include recombinantly produced MaSp1 (also known as MaSpI), and MaSp2 (also known as MaSpII) proteins, including repeats of each of these which contain 8 units thereof and are encoded by DNA of SEQ ID NO: 3 and SEQ ID NO: 4, respectively; minor ampullate spider silk proteins; flagelliform silks; and spider silk proteins described in any of U.S. Pat. Nos. 5,989,894; 5,728,810; 5,756,677; 5,733,771; 5,994,099; 7,057,023; and U.S. provisional patent application No. 60/315,529 (all of which are incorporated herein by reference).

In other embodiments, a vector system in accordance with the principles of the present invention may contain a sequence that encodes for silk peptides A-H as listed hereafter. A vector system is said to contain a sequence that encodes for a protein or peptide sequence when it contains DNA made up of a series of codons which, when transcribed and translated, will result in a polypeptide of that sequence. Any codon representing a particular amino acid may be used. The peptide sequences are listed in Table 1.

TABLE 1

| PEPTIDE | AMINO ACID SEQUENCE |
|---|---|
| A | (GPGGX)$_n$; X = any of A, S, Q, or Y; n = 1 to 65 inclusive |
| B | (GGZ)$_m$; Z = any of A, Q, Y, T, or V; n = 1 to 35 inclusive |
| C | A$_h$; h = 2-16 inclusive; S can substitute for A for up to 25% of the total sequence |
| D | (GB)$_j$; B = any of A, S, Q, P, with A preferred; j = 1-10 inclusive |
| E | GPXGPGX; X = A or S |
| F | (QQSSVAQS)$_p$; p = 1-60 inclusive (SEQ ID NO: 35) |

TABLE 1-continued

| PEPTIDE | AMINO ACID SEQUENCE |
|---|---|
| G | (RPLPARRPLPAPLPAPRPIPAPLPRPVPI)$_a$; a = 1-60 inclusive (SEQ ID NO: 36) |
| H | THEDLDITIDGADOPITISEELTISGAGGS (SEQ ID NO: 34) |

For peptides A, B, and D, the amino acids at the position where substitution is to be made can all be the same amino acid for each repeat, or can vary independently from one another.

The sequences can be arranged in a large number of ways. Example sequences using the peptides of the table above include, but are not limited to, ABC, ABCD, ABCE, ABCDE, A, B, BC, BCD, BD, BDC, E, ABE, AB, F, G, H, and GF. As mentioned previously, use of any combination of DNA sequence which encodes for a peptide sequence as detailed above in a vector system falls within the scope of the present invention.

In other embodiments, synthetic sequences based on MaSp1 and MaSp2 can be encoded by a vector. These include the sequences of Table 2:

TABLE 2

| SEQ ID NO: 20 | GGAGQGGYGGQGAGQGGYGGLGSQGAGRGGLGGQG AGAAAAAAAA |
|---|---|
| SEQ ID NO: 21 | SGPGQQGPGGYGPGQQGPGGYGPGQQGPSGPGSAA AAAAAA |
| SEQ ID NO: 22 | GGAGQGGYGGLGSQGAGRGGLGGQ |
| SEQ ID NO: 23 | GPGGYGPGQQGPSGPGSAAAAGPSGPGSAAAA |
| SEQ ID NO: 24 | GPGGYGPGQQGPGSQGPGSGGQQGPGGQGPYGPSAA AAAAAA |
| SEQ ID NO: 25 | PGGGGAGQGGYGGLGSQGAGRGGLGGQGAGAAAAAA GPGGYGPGQQGPSGPGSAAAAAAAA |

In other embodiments, synthetic sequences based on flagelliform and MaSp2 can be encoded by a vector. These include the sequences of Table 3:

TABLE 3

| SEQ ID NO: 26 | GPGGAGPGGAGPGGAGPGGA |
|---|---|
| SEQ ID NO: 27 | GPGGAGPGGAGPGGAGPGGAGPSGPGSAAAAAAAA |
| SEQ ID NO: 28 | GPGGYGPGGSGPGGYGPGGSGPSGPGSAAAAAAAA |
| SEQ ID NO: 29 | GGAGGSGGAGGSGGVGGSGGT |
| SEQ ID NO: 30 | GGAGGSGGAGGSGGVGGSGGTGPGGSGPGGYGPGG SGPGGYGPGGSGPGGYGPGGSGPGGYGPGGSGPGG YGPGGSGPGGYGPGGSGPGGYGPGGSGPGGY |
| SEQ ID NO: 31 | GGAGGSGGAGGSGGVGGSGGTTIEDLDITIDGADG PITISEELTISGAGGS |
| SEQ ID NO: 32 | GGAGGSGGAGGSGGVGGSGEITGPGGSGPGGYGPG GSGPGGYGPGGSGPGGYGPGGSGPGGYGPGGSGPG GYGPGGSGPGGYGPGGSGPGGYGPGGSGPGGYTTI EDLDITIDGADGPITISEELTISGAGGS |
| SEQ ID NO: 33 | GGAGGSGGAGGSGGVGGSGGTGPGGSGPGGYGPG GSGPGGYGPGGSGPGGYGPGGSGPGGYGPGGSGP GGYGPGGSGPGGYGPGGSGPGGYGPGGSGPGGYT TIEDLDITIDGADGPITISEELTISGAGGSGPGG PAAAAA |

In the cases of SEQ ID NO: 27 and SEQ ID NO: 28, the sequences GPGGAGPGGAGPGGAGPGGA (SEQ ID NO: 26) and GPGGYGPGGSGPGGYGPGGS (SEQ ID NO: 39), respectively, may occur once, twice, three times, or four times end-to-end.

The sequences of the spider silk proteins may have amino acid inserts or terminal additions, so long as the protein retains the desired physical characteristics. Likewise, some of the amino acid sequences may be deleted from the protein so long as the protein retains the desired physical characteristics. Amino acid substitutions may also be made in the sequences, so long as the protein possesses or retains the desired physical characteristics.

In one embodiment, protein production can be achieved using bioreactors. For instance, fed-batch culture growths can be conducted in New Brunswick Scientific (Endfield, Conn., USA) Bioflo 115 (3 L), Bioflo 310 (5 L) or Bioflo 610 (100 L) controller bioreactors with BioCommand software.

Culture medium for growth of bacterial culture inocula can be composed of, per liter: 2 g $KH_2PO_4$, 4 g $K_2HPO_4.3H_2O$, 5 g $(NH_4)2HPO_4$, 5 g Yeast Extract, 5 g Hy Express System II (YE-HY ES II, Sheffield™ Bio-Science, Norwich, N.Y.), 25 g glucose, 0.5 g $MgSO_4.7H_2O$, 2.5 mg Thiamine and 5 ml trace metal solution A (1.25 mL 6N $H_2SO_4$, 0.5 g NaCl, 0.1 g $ZnSO_4.7H_2O$, 0.4 g $MnCl_2.4H_2O$, 0.48 g $FeCl_3.6H_2O$, 0.04 g $CuSO_4.5H_2O$, 0.058 g $H_3BO_3$, 0.05 g $NaMoO_4.2H_2O$ in distilled water to a final volume of 100 mL). All culture media may contain kanamycin (50 or 100 µg/mL) and/or chloramphenicol (60 or 120 µg/mL.)

Seed medium can be prepared in a liter bottle containing, for example, 5 g Yeast Extract, 15 g Hy Express System II, 16 g glycerol, 25 g glucose, 3.3 g $(NH4)2SO4$, 6.8 g $KH_2PO_4$, 7.1 g $Na_2HPO_4$, 1.5 mL trace element B solution (0.3 mL 6N $H_2SO_4$, 0.25 g $CuSO_4.5H_2$, 2.4 g MsSO4, 0.30 g $NaMoO_4. 2H_2O$, 2.5 g $Ni(NO_3)_2$, 1.5 g ZnSO4 in 100 mL distilled water) and 1.5 mL trace element C solution (0.5 g NaCl, 0.475 g $FeCl_3.6H_2O$, 0.075 g $CoCl_2.6H_2O$, 0.050 g $H_3BO_3$, 0.29 g $CaCl_2.2H_2O$ in 100 mL distilled water).

Glucose feeding solution may include, per liter: 500 g glucose, 200 ml 5% Hy Express System II (Sheffield™ Bio-Science, Norwich, N.Y.), 10 g $MgSO_4.7H_2O$, 40 mg Thiamine and 5 ml trace metal solution A (1.25 mL 6N $H_2SO_4$, 0.5 g NaCl, 0.1 g $ZnSO_4.7H_2O$, 0.4 g $MnCl_2.4H_2O$, 0.48 g $FeCl_3.6H_2O$, 0.04 g $CuSO_4.5H_2O$, 0.058 g $H_3BO_3$, 0.05 g $NaMoO_4.2H_2O$ in distilled water to a final volume of 100 mL). In one embodiment, whenever the fermentation culture is supplemented with additional glucose feeding solution, an aminoglycoside compound, such as for example kanamycin at about 1 to about 300 micrograms per milliliter, more preferably about 25 to about 100 micrograms per milliliter, is added as well. The addition of this compound increases expression of protein.

Starter cultures may be grown from colonies in 2 mL of YE-HY ES II at 37° C. for 6 hours and later cultivated for another 6 hours on a rotary shaker at 220 rpm, until the $OD_{600}$ is ~3-5 before addition to a fermenter. Fed-batch cultures can be carried out at 37° C. in the fermenters. The inoculum cultures are added with 5-10% (v/v) inoculation size. The culture media may contain kanamycin (50 or 100 µg/mL).

In some cases, two seed cultures may be used. For the first seed culture, BL21(DE3) bacterial colonies harboring pET19-SXT (SEQ ID NO: 7); pET19kT (SEQ ID NO: 6) and p4GPP; or pET19kTPP-4GPP may be inoculated into 10 ml of YE-Hy ES II media with, taking into account appropriate antibiotic resistances, about 100 micrograms per milliliter of kanamycin, about 60 micrograms per milliliter of chloramphenicol, or both, and cultured at about 37° C. for about 5 hours. In a second seed culture step, about 10 milliliters of the first seed culture are inoculated into about 100 ml of YE-Hy ES II media, and cultured at about 37° C. for about 5 hours, to a final $OD_{600}$ about between about 2 and about 3.

Significantly, culture pH is monitored and can be controlled at 6.9 to 7.0 by the addition of 20% (vol/vol) ammonia solution. The use of an ammonia solution served to improve protein yields in the final purification by up to 10-fold. This represents an unexpectedly large increase of yield. Without wishing to be bound by any particular theory, adding a nitrogen source during fermentation increased the amount of recombinant spider silk constructs recovered.

The dissolved oxygen concentration is controlled at 45% of air saturation by automatically increasing the agitation speed up to 450 to 900 rpm (depending on the fermenters) and by changing the pure oxygen percentage. Levels of glucose are monitored (15-30 g/L) using diabetic glucose test strips throughout the run. In one embodiment, when the glucose level is below a predetermined threshold of for example 15 g/L, a computerized operator adjusts the exponential feed-line to supplement the bacteria. Such supplementation can be accompanied by the addition of an aminoglycoside compound, such as kanamycin at about 1 to about 300 micrograms per milliliter, more preferably about 25 to about 100 micrograms per milliliter.

Figure 6:
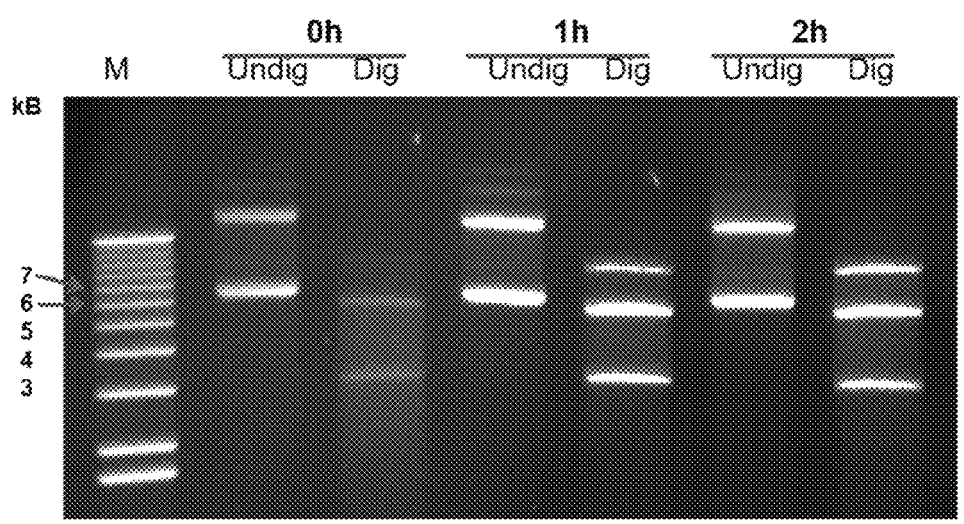
FIG. 6 is an image of an agarose gel illustrating the effect of providing an aminoglycoside compound to an induced culture on plasmid retention.

Gene expression was induced at an optical density of $OD_{600}$~80 by reducing the temperature to 25° C. and adding an inducer, such as 1 mM isopropyl β-D-1-thiogalactopyranoside (IPTG). Other inducers include maltose, lactose, rhamnose, and other sugars. In some cases, the inducer can be a spike in heat in order to elicit a heat shock response. When the inducer is added, the culture may be supplemented with an aminoglycoside compound, particularly kanamycinin in a quantity of 200 g/mL. In some embodiments, the inducer and antibiotic may be added simultaneously. The term "simultaneously" or "simultaneous" as used herein means at or around the same time. Fermentation continued for an additional about 2 to about 16 hours, preferably about 4 to about 16 hours, before harvesting by centrifugation. Surprisingly, addition of the aminoglycoside compound increased protein yield greatly, in some cases up to 75%. As seen in FIG. 6, it is believed that the increase is realized owing to the maintenance of greater numbers of copies of the expression vectors of the vector system.

Figure 2:
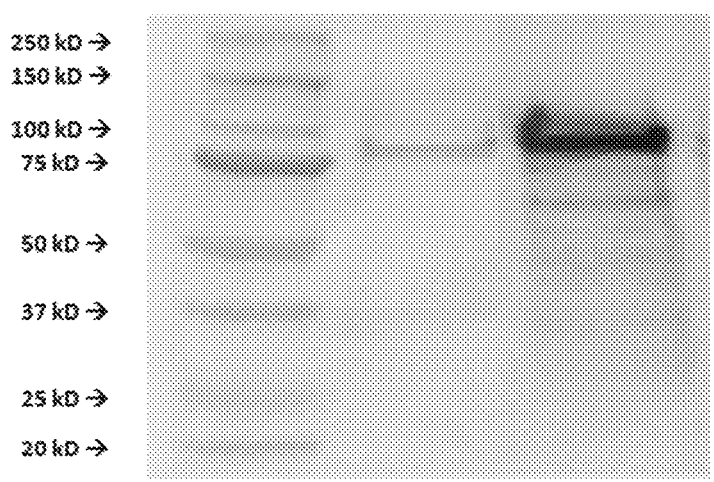
FIG. 2 is a growth curve of E. coli BL21 transformed with a vector constructed in accordance with the principles of the present disclosure.
Figure 3:
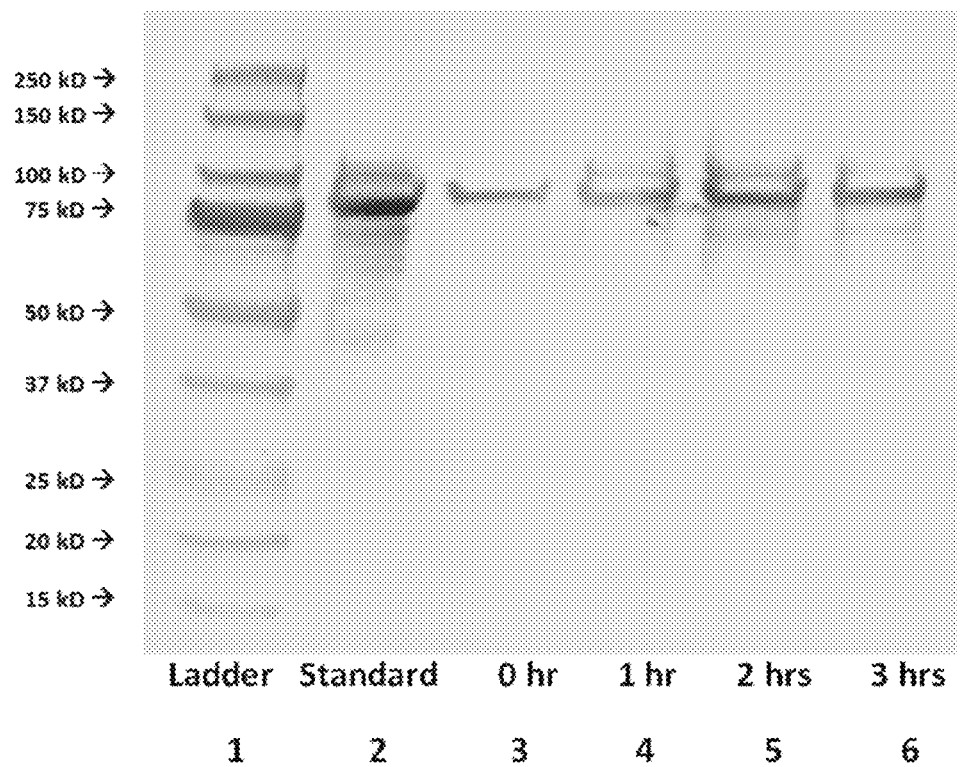
FIG. 3 is an image of an electrophoretic gel showing relative levels of expression between a normal pET19K expression vector and a vector system in accordance with the principles of the present disclosure.

With the fermentation protocol disclosed herein, *E. coli* transformed with an expression vector as described can be grown to high cell density ($OD_{600}$ of about 120, FIG. 2). *E. coli* with pET19K-SX-FLYS$_3$ vector produced more spider silk protein than *E. coli* with pET19K-FLYS$_3$, as shown in FIG. 3. Further, a two-vector (pET19kTPP/p4GPP) system shows increased expression of FLYS$_6$ compared to a single-vector (pET-SXT) system (see Example 5 and FIG. 9.)

Figure 4:
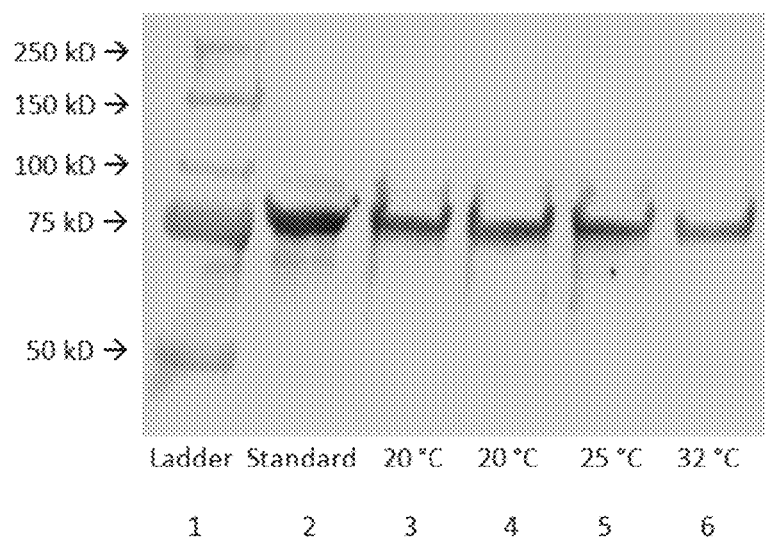
FIG. 4 is an image of an electrophoretic gel showing relative levels of expression between induced cultures using a vector system in accordance with the principles of the present disclosure at different induction temperatures.
Figure 5:
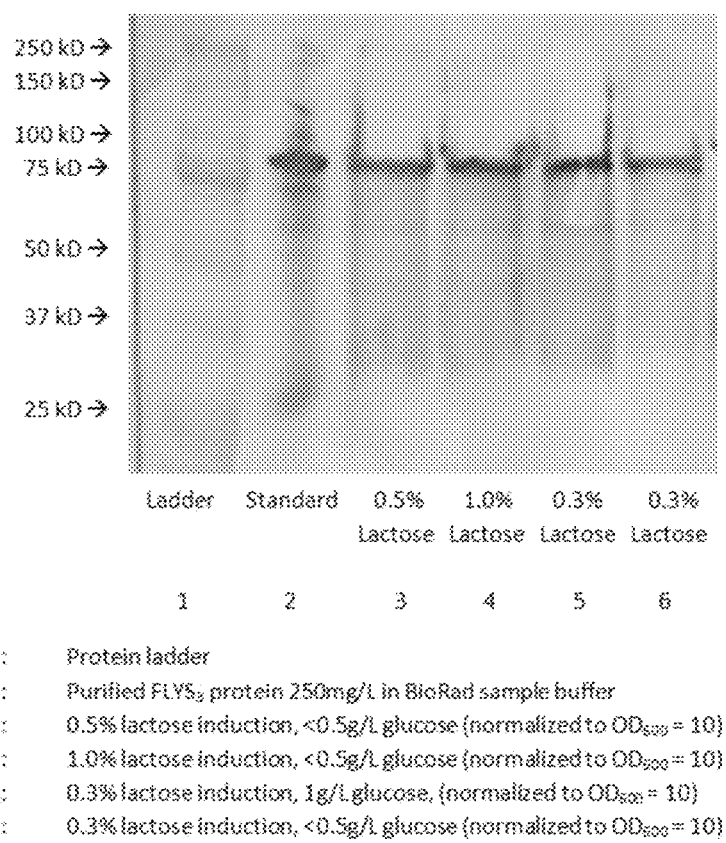
FIG. 5 is an image of an electrophoretic gel showing relative levels of expression between induced cultures using a vector system in accordance with the principles of the present disclosure illustrating that lactose can drive expression.
Figure 7:
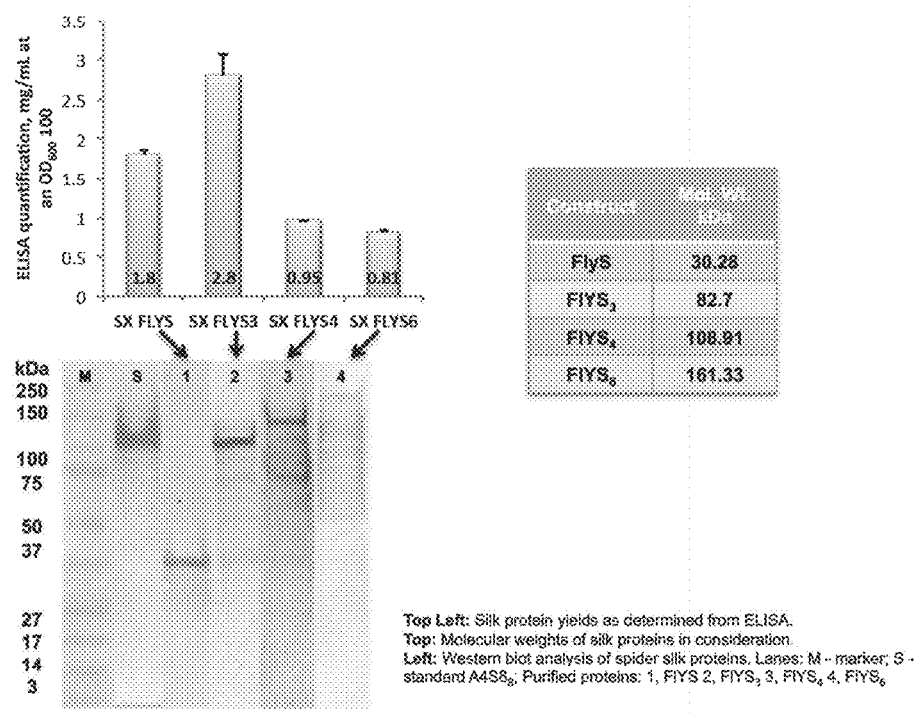
FIG. 7 is an analysis of the expression of protein and quantification of spider silk proteins produced thereby.

In the pET19K-FLYS$_3$ expression trial, there was a leaky protein expression before IPTG induction, but after two hours induction, spider silk protein expression reached a much higher level. Induction at lower temperature (20-25° C.) produced more spider silk protein of a higher proportion of full-length protein than at higher temperature (32° C.) (FIG. 4). Lactose can be used to induce spider silk protein expression, but less spider silk protein is produced than with IPTG induction (FIG. 5). Addition of an aminoglycoside compound, such as kanamycin, at and after induction, assists in preventing loss of plasmid, and thus increasing expression, at high ODs (FIG. 6). After extraction and purification, at least 0.5 g/L pure spider silk protein from *E. coli* fermentation can be produced (FIG. 7).

The following examples are illustrative only and are not intended to limit the disclosure in any way.

EXAMPLES

Example 1

Vector system including two vectors. Two two-vector systems were developed for expression of spider silk proteins in bacteria. Each vector system made use of the vector p4GPP, which contains the gene cassettes glyT, proL, proM, and glyVXY. These cassettes provide additional tRNAs which become charged with glycine and proline. The first two-vector system also included pET19kT. pET19kT encodes a non-repetitive sequence of one hundred amino acids at the C-terminus of a protein expressed when its expression gene has been inserted at the multiple cloning site. The second two-vector system includes p4GPP and pET19kTPP. pET19kTPP was generated by replacing the serine and glycine residues after the 10× His-tag with two valine and six proline residues to make the His-tag more accessible.

Example 2

Vector system including a single vector. pET19-SXT from pET19k by incorporating the C-terminal, non-repetitive sequence and the gene that results in the expression of serine hydroxyl methyltransferase (SHMT) (which converts the amino acid serine to glycine) along with sequences that produce additional tRNAs for glycine and proline, as in EXAMPLE 1.

Example 3

Cloning of silk modules into vectors. The 1.1 kbp monomer gene was synthesized in pMA-RQ vector by GeneArt® (Life Technologies, Carlsbad, Calif.) to contain the consensus motif of naturally occurring highly repetitive spider silk-like sequences from the golden orb weaving spider *Nephila clavipes*. The complete monomer sequence (FlAS or FlYS) is comprised of the coding sequences for flagelliform, silk-like putative elastic motif, GPGGX1GPGGX2 (X1/X2=A/A for FlAS, X1/X2=Y/S for FlYS) combined with the major ampullate 2 silk-like putative strength motif, linker-polyalanine—GGPSGPGSA$_8$ (SEQ ID NO: 38). Multimers of (FlAS)$_n$ or (FlYS)$_n$ were generated by recombinant DNA technology using a compatible but non-regenerable cloning strategy. The restriction sites used were 5'-XmaI and 3'-BspEI in combination with a unique restriction site (PvuI) on the pMA-RQ vector. The PvuI-XmaI and PvuI-BspEI fragments, each containing one copy of the cloned monomer sequence, were ligated together, thus, effectively regenerating a full plasmid while doubling the size of the monomer insert in the process. The regenerated plasmid containing the silk insert was cloned into bacteria and used as a template in the next cloning step. After repeated rounds of cloning, this strategy increased the size of the silk-like insert to the desired number of motif repeats. For FlAS or FlYS, the motif was repeated 2, 3, 4, and 8 times. Once the desired size of insert was achieved through the outlined steps above, the synthetic spider silk gene is released from the recombinant pMA-RQ vector by restriction digestion in 5' with NdeI and in 3' by BamHI. The purified insert as cloned in frame into the expression vector (pET19kT and pET19-SXT) at the NdeI/BamHI sites for expression of the protein. Cloning of the multimer (FLAS)n or (FlYS)n was confirmed by partially sequencing using vector specific primers. The same cloning strategy was also followed for MaSp 1, MaSp2 and MiSp, including MiSp8 which is encoded by SEQ ID NO: 2.

Example 4

Expression of spider silk constructs of different sizes in BL21(DE3) are shown in FIG. 8. FlYS4 and FlAS6 constructs were expressed in a pET19kT/4GPP two-vector system and a time course study was undertaken. Lane 1 of each depicted gel is a protein ladder with molecular weights indicated; lane 2 is a purified FLYS3 construct for reference; in lanes 3-10, odd numbered lanes are supernatant fractions and even numbered lanes are pellet fractions. Lanes 3-4 are uninduced cultures; lanes 5-6 are 1 hour after IPTG induction; lanes 7-8 are 3 hours after IPTG induction; lanes 9-10 are 4 hours after IPTG induction. Cultures were normalized to OD600=10 and run on an electrophoretic gel.

Example 5

Comparison of expression of FLYS6 construct in one- and two-vector systems. FIG. 9A depicts expression of FLYS6 in a two-vector (pET19kTPP/p4GPP) system, and FIG. 9B depicts expression of FLYS6 in a single-vector (pET-SXT) system. Lane 1 of each depicted gel is a protein ladder with molecular weights indicated; lane 2 is a purified FLYS3 construct for reference. Lanes 3 are uninduced cultures; lanes 4 are 1 hour after IPTG induction; lanes 5 are 2 hours after IPTG induction; lanes 6 are 3 hours after IPTG induction; lanes 7 are 4 hours after IPTG induction. Comparison of any of lanes 4-7 reveals increased expression of silk protein by the two-vector system relative to the single-vector system.

Example 6

Comparison of induction temperatures and protein expression levels. FIG. 10A shows induction by IPTG of FLAS4 in a two-vector system at 25° C.; FIG. 10B shows induction of the same construct in the same vector system by IPTG at 16° C. Lane 1 of each depicted gel is a protein ladder with molecular weights indicated; lane 2 is a purified FLYS3 construct for reference. Lanes 3 are uninduced cultures; lanes 4 are 1 hour after IPTG induction; lanes 5 are 2 hours after IPTG induction; lanes 6 are 3 hours after IPTG induction; lanes 7 are 4 hours after IPTG induction. Comparison of any of lanes 5-7 reveals increased expression of silk protein at the lower temperature relative to the 25 degree fermentation. Samples were normalized to OD$_{600}$=about 10.

Example 7

Protein expression and estimated yields. A variety of spider silk constructs were expressed in single- and two-vector systems, and at different induction systems, and their expression systems analyzed by enzyme linked immunosorbent assay (ELISA). FLYS2 in single vector SXT induced at 25° C. and FLYS3 in double vector pET19kT/p4GPP induced at 25° C. yielded about 0.325 mg/ml; larger construct FLYS6 in single vector SXT induced at 16° C. yielded about 0.050 mg/ml protein, as did FLAS4 and FLAS6 in double vector pET19kT/p4GPP system, induced at 25° C.

each. FLAS4 in double vector pET19kT/p4GPP yielded nearly 0.1 mg/ml when induction temperature was decreased to 16° C.

Expression of spider silk protein production is carried out by changing protein induction temperature and antibiotic (aminoglycoside, specifically kanamycin) concentration. The expression of spider silk protein is induced at 20°, 25°, 30°, 32° and 37° C. The role of kanamycin in the protein production was studied at 100 µg/mL, 200 µg/mL, 300 µg/mL and 400 µg/mL of kanamycin. In the study *E. coli* with pET19K-SX-FLYS$_3$ was induced at high OD$_{600}$. Samples were taken at 0 hour, 1 hour and 2 hours after induction. Samples taken at different time points were normalized to an OD$_{600}$=5. Regarding FIG. 5, plasmids were extracted, purified and digested with restriction enzymes NdeI/BamHI to check presence of silk insert before (0 h) and after induction (1 h, 2 h).

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

In the following part of the present specification, numbered examples are listed which are directed to and which define advantageous embodiments. Said examples and embodiments belong to the present disclosure and description. The embodiments, examples, and features as listed, can separately or in groups, be combined in any manner to form embodiments belonging to the present disclosure.

Numbered examples: 1. A method of producing a synthetic spider silk, comprising: transforming one or more bacterial cells with an expression vector system comprising a first antibiotic resistance gene, a spider silk protein-encoding open reading frame, and a transfer RNA gene, to generate transformed bacterial cells; fermenting the transformed bacterial cells in a culture medium; inducing spider silk protein expression in the cultured *E. coli* with an inducer, and purifying the synthetic spider silk protein.

2. The method of example 1, wherein the expression vector system consists of a single vector.

3. The method of any one of examples 1-2, wherein the expression vector system comprises more than one type of vector, the first antibiotic resistance gene and the spider silk protein-encoding open reading frame residing on a first vector, and the transfer RNA gene and a second resistance gene to a second antibiotic residing on a second vector.

4. The method of any one of examples 1-3, wherein the spider silk protein-encoding open reading frame encodes at least one of flagelliform silk, MaSp 1, MaSp2, MiSp, or a combination thereof.

5. The method of any one of examples 1-4, wherein the protein-encoding open reading frame comprises sequence coding for a C-terminal tail.

6. The method of any one of examples 1-5, wherein inducing spider silk protein expression comprises holding the fermentation temperature within a temperature range of from about 20° C. to about 25° C.

7. The method of any one of examples 1-6, wherein the inducer is selected from the group consisting of isopropyl 3-D-1-thiogalactopyranoside, lactose, maltose, rhamnose, and another sugar-based induction system.

8. The method of any one of examples 1-6, wherein the inducer is a heat shock step.

9. The method of any one of examples 1-8, wherein inducing spider silk protein expression comprises simultaneously adding the inducer and an antibiotic to which the first antibiotic resistance gene provides resistance.

10. The method according to examples any one of claims 1-9 wherein the antibiotic is an aminoglycoside antibiotic.

11. The method of any one of examples 1-10, wherein the aminoglycoside antibiotic is selected from the group consisting of: a kanamycin, a neomycin, streptomycin, amikacin, tobramycin, dibekacin, gentamycin, sisomicin, and netilmicin.

12. The method of any one of examples 1-11, wherein the aminoglycoside antibiotic is kanamycin.

13. The method of any one of examples 1-12, further comprising monitoring a level of glucose in the culture medium, and supplementing the culture medium with glucose and an antibiotic when the glucose level falls below a predetermined threshold amount.

14. The method of any one of examples 1-13, further comprising monitoring a pH of the culture medium, and adjusting the pH of the culture medium with a nitrogen-containing base when the pH falls below a predetermined threshold amount.

15. The method of any one of examples 1-15, wherein the nitrogen-containing base is ammonium hydroxide.

16. A DNA vector system for expressing spider silk proteins in bacteria comprising: a first antibiotic resistance gene, a spider silk protein-encoding open reading frame, and a transfer RNA gene.

17. The vector system of example 16, wherein the spider silk protein-encoding open reading frame encodes for at least one of flagelliform silk, MaSp 1, MaSp2, MiSp, or a combination thereof.

18. The vector system of any one of examples 16-17, wherein the transfer RNA gene encodes for a glycine-bearing transfer RNA.

19. The vector system of any one of examples 16-18, wherein all of the resistance gene to the first antibiotic, the spider silk protein-encoding open reading frame, and a transfer RNA gene reside on a single DNA vector.

20. The vector system of any one of examples 16-19, wherein the resistance gene to the first antibiotic and the spider silk protein-encoding open reading frame reside on a first vector, and the transfer RNA gene resides on a second vector with a resistance gene to a second antibiotic.

What is claimed is:

1. A method of producing a synthetic spider silk, comprising:
   transforming one or more bacterial cells with an expression vector system comprising a first antibiotic resistance gene, a spider silk protein-encoding open reading frame, and a transfer RNA gene, to generate transformed bacterial cells;
   fermenting the transformed bacterial cells in a culture medium;
   inducing spider silk protein expression in the cultured *E. coli* with an inducer, wherein the inducing spider silk protein expression comprises holding the fermentation temperature within a temperature range of from about 20° C. to about 25° C.; and
   purifying the synthetic spider silk protein.

2. The method of claim 1, wherein the expression vector system consists of a single vector.

3. The method of claim 1, wherein the expression vector system comprises more than one type of vector, the first antibiotic resistance gene and the spider silk protein-encoding open reading frame residing on a first vector, and the transfer RNA gene and a second resistance gene to a second antibiotic residing on a second vector.

4. The method of claim 1, wherein the spider silk protein-encoding open reading frame encodes at least one of flagelliform silk, MaSp 1, MaSp2, MiSp, or a combination thereof.

5. The method of claim 1, wherein the protein-encoding open reading frame comprises sequence coding for a C-terminal tail.

6. The method of claim 1, wherein the inducer is selected from the group consisting of isopropyl β-D-1-thiogalactopyranoside, lactose, maltose, and rhamnose.

7. The method of claim 1, wherein the inducer is a heat shock step.

8. The method of claim 1, wherein inducing spider silk protein expression comprises simultaneously adding the inducer and an antibiotic to which the first antibiotic resistance gene provides resistance.

9. The method of claim 1, wherein the antibiotic is an aminoglycoside antibiotic.

10. The method of claim 9, wherein the aminoglycoside antibiotic is selected from the group consisting of: a kanamycin, a neomycin, streptomycin, amikacin, tobramycin, dibekacin, gentamycin, sisomicin, and netilmicin.

11. The method of claim 9, wherein the aminoglycoside antibiotic is kanamycin.

12. The method of claim 1, further comprising monitoring a level of glucose in the culture medium, and supplementing the culture medium with glucose and an antibiotic when the glucose level falls below a predetermined threshold amount.

13. The method of claim 1, further comprising monitoring a pH of the culture medium, and adjusting the pH of the culture medium with a nitrogen-containing base when the pH falls below a predetermined threshold amount.

14. The method of claim 13, wherein the nitrogen-containing base is ammonium hydroxide.

* * * * *